US011766298B2

United States Patent
Glossop

(10) Patent No.: US 11,766,298 B2
(45) Date of Patent: Sep. 26, 2023

(54) SYSTEMS, METHODS, AND DEVICES FOR REGISTERING AND TRACKING ORGANS DURING INTERVENTIONAL PROCEDURES

(71) Applicant: Neil Glossop, Toronto (CA)

(72) Inventor: Neil Glossop, Toronto (CA)

( * ) Notice: Subject to any disclaimer, the term of this patent is extended or adjusted under 35 U.S.C. 154(b) by 111 days.

(21) Appl. No.: 16/697,357

(22) Filed: Nov. 27, 2019

(65) Prior Publication Data

US 2020/0345426 A1 Nov. 5, 2020

Related U.S. Application Data

(60) Provisional application No. 62/842,863, filed on May 3, 2019.

(51) Int. Cl.
*A61B 34/20* (2016.01)
*A61B 8/08* (2006.01)
(Continued)

(52) U.S. Cl.
CPC .............. *A61B 34/20* (2016.02); *A61B 1/307* (2013.01); *A61B 8/0841* (2013.01); *A61B 8/12* (2013.01);
(Continued)

(58) Field of Classification Search
CPC ....... A61B 90/39; A61B 1/307; A61B 8/0841; A61B 8/12; A61B 2034/102; A61B 2034/105; A61B 2034/107; A61B 2034/2063; A61B 2034/2065; A61B 2090/3925; A61B 2090/3966;
(Continued)

(56) References Cited

U.S. PATENT DOCUMENTS 3,867,945 A 2/1975 Long
5,081,997 A 1/1992 Bosley, Jr.
(Continued)

OTHER PUBLICATIONS

Hu, Xiaohua, et al., "Steerable Catheters for Minimally Invasive Surgery: A Review and Future Directions", Computer Assisted Surgery, vol. 23, No. 1, DOI: 10.1080/24699322.2018.1526972, (Year: 2018), pp. 21-41.
(Continued)

*Primary Examiner* — John Denny Li
(74) *Attorney, Agent, or Firm* — Sheppard Mullin Richter & Hampton LLP

(57) ABSTRACT

Systems, methods, and devices are provided for assisting or performing guided interventional procedures using. The system uses pre-procedure scans of a patient's anatomy to identify targets and critical structures. A measurement device containing position indicating elements or fiducials is placed in a pre-existing or physician created conduit or lumen whose geometry is known from a scan. During a procedure, the pre-procedure scans may be registered to the patient using the position indicating elements or fiducials and the geometry of the conduit. This registration may be used in an intervention to guide instruments that can obtain diagnostic information or provide therapy to the identified targets. During the procedure, the position indicating elements may be used to dynamically compensate for motion to further improve accuracy.

24 Claims, 15 Drawing Sheets

(51) Int. Cl.
  *A61M 25/10* (2013.01)
  *A61M 25/00* (2006.01)
  *A61B 1/307* (2006.01)
  *A61B 90/00* (2016.01)
  *A61B 34/10* (2016.01)
  *A61B 8/12* (2006.01)

(52) U.S. Cl.
  CPC ............ *A61B 34/10* (2016.02); *A61B 90/39* (2016.02); *A61M 25/0017* (2013.01); *A61M 25/10* (2013.01); *A61B 2034/102* (2016.02); *A61B 2034/105* (2016.02); *A61B 2034/107* (2016.02); *A61B 2034/2063* (2016.02); *A61B 2034/2065* (2016.02); *A61B 2090/3925* (2016.02); *A61B 2090/3966* (2016.02); *A61B 2090/3983* (2016.02)

(58) Field of Classification Search
  CPC ... A61B 2090/3983; A61B 2017/3411; A61M 25/0017; A61M 25/10; A61N 2005/1012
  See application file for complete search history.

(56) References Cited

U.S. PATENT DOCUMENTS

| | | | |
|---|---|---|---|
| 5,112,268 | A | 5/1992 | Klaus |
| 5,133,684 | A | 7/1992 | Rhodes |
| 5,409,444 | A | 4/1995 | Kensey |
| 5,558,091 | A | 9/1996 | Acker |
| 5,868,673 | A | 2/1999 | Vesely |
| 6,073,043 | A | 6/2000 | Schneider |
| 6,139,544 | A | 10/2000 | Mikus |
| 6,245,029 | B1 | 6/2001 | Fujita |
| 6,266,552 | B1 | 7/2001 | Slettenmark |
| D466,609 | S | 12/2002 | Glossop |
| 6,754,376 | B1 | 6/2004 | Turek |
| 6,785,571 | B2 | 8/2004 | Glossop |
| 7,697,972 | B2 | 4/2010 | Verard |
| 7,751,868 | B2 | 7/2010 | Glossop |
| 7,840,254 | B2 | 11/2010 | Glossop |
| 7,881,769 | B2 | 2/2011 | Sobe |
| 8,046,052 | B2 | 10/2011 | Verard |
| 8,073,529 | B2 | 12/2011 | Cermak |
| 8,315,690 | B2 | 11/2012 | Groszmann |
| 8,625,865 | B2 | 1/2014 | Zarkh |
| 8,811,777 | B2 | 8/2014 | Younge |
| 8,948,845 | B2 | 2/2015 | Glossop |
| 8,956,364 | B2 | 2/2015 | Catanzarite |
| 9,392,960 | B2 | 7/2016 | Zvuloni |
| 9,655,595 | B2 | 5/2017 | Glossop |
| 9,681,919 | B2 | 6/2017 | Glossop |
| 10,265,137 | B2 | 4/2019 | Glossop |
| 10,369,384 | B2 | 8/2019 | Kung |
| 10,524,693 | B2 | 1/2020 | Freysinger |
| 10,706,543 | B2 | 7/2020 | Donhowe |
| 2005/0182319 | A1 | 8/2005 | Glossop |
| 2008/0269684 | A1 | 10/2008 | Anderson |
| 2009/0093702 | A1* | 4/2009 | Vollmer ................. A61B 5/064 600/407 |
| 2009/0221908 | A1 | 9/2009 | Glossop |
| 2011/0178394 | A1* | 7/2011 | Fitzpatrick ................ G06T 7/33 600/424 |
| 2012/0027278 | A1* | 2/2012 | Chaney ................. G06T 7/149 382/131 |
| 2013/0079628 | A1 | 3/2013 | Groszmann |
| 2013/0090554 | A1 | 4/2013 | Zvuloni |
| 2013/0331686 | A1* | 12/2013 | Freysinger ............. A61B 34/20 600/417 |
| 2014/0034800 | A1* | 2/2014 | Strong ..................... A61B 8/12 248/299.1 |
| 2014/0321710 | A1* | 10/2014 | Robert ................... A61B 34/20 382/103 |
| 2015/0216532 | A1* | 8/2015 | Hlavka .......... A61B 17/320016 606/192 |
| 2015/0216619 | A1 | 8/2015 | Kruecker |
| 2016/0008074 | A1* | 1/2016 | Glossop ............. A61B 17/0218 606/130 |
| 2016/0367168 | A1* | 12/2016 | Malinin ................. A61B 5/066 |
| 2017/0020623 | A1 | 1/2017 | Glossop |
| 2017/0079554 | A1* | 3/2017 | Glossop ............... A61B 6/5247 |
| 2018/0235709 | A1 | 8/2018 | Donhowe |
| 2018/0369541 | A1* | 12/2018 | Braun ..................... A61B 90/39 |
| 2019/0069959 | A1 | 3/2019 | Palushi |
| 2020/0093498 | A1 | 3/2020 | Roberts |
| 2020/0281660 | A1* | 9/2020 | Homan .................. G06V 40/19 |
| 2020/0345426 | A1 | 11/2020 | Glossop |

OTHER PUBLICATIONS

Morris, Karcher, et al., "Design of an Esophageal Deflection Device for Use During Atrial Ablation Procedures", Journal of Materials Research and Technology, vol. 9, Issue 6, Nov.-Dec. 2020, DOI: 10.1016/j.imrt.2020.09.123, pp. 13801-13812.

Arun, K. S., et al., "Least-Squares Fitting of Two 3-D Point Sets", IEEE Transactions on Pattern Analysis and Machine Intelligence, vol. PAMI-9, No. 5, Sep. 1987, pp. 698-700, DOI: 10.1109/TPAMI.1987.4767965.

Fitzpatrick, J. Michael, et al., "The Distribution of Target Registration Error in Rigid-Body Point-Based Registration", IEEE Transactions on Medical Imaging, vol. 20, No. 9, Sep. 2001, pp. 917-927, DOI: 10.1109/42.952729.

Gee, A. H., et al., "3D Ultrasound Probe Calibration Without a Position Sensor," CUED/FINFENG/TR 488, Sep. 2004, Cambridge University, Department of Engineering, <URL: http://mi.eng.cam.ac.uk/reports/svr-ftp/gee_tr488.pdf>, accessed Jun. 11, 2019, 21 pages.

Gruen, Armin, et al., "Least Squares 3D Surface and Curve Matching", ISPRS Journal of Photogrammetry & Remote Sensing, vol. 59, 2005, pp. 151-174, DOI: 10.1016/j.isprsjprs.2005.02.006.

Lindseth, Frank, et al., "Probe Calibration for Freehand 3-D Ultrasound", Ultrasound in Med. & Biol., vol. 29, No. 11, pp. 1607-1623, Nov. 2003, DOI: 10.1016/S0301-5629(03)01012-3.

Pinto, Peter A., et al., "Magnetic Resonance Imaging/Ultrasound Fusion Guided Prostate Biopsy Improves Cancer Detection Following Transrectal Ultrasound Biopsy and Correlates with Multiparametric Magnetic Resonance Imaging," The Journal of Urology, vol. 186, Issue 4, Oct. 2011, pp. 1281-1285, DOI: 10.1016/j.juro.2011.05.078.

Tagliasacchi, Andrea, et al., "Mean Curvature Skeletons", Eurographics Symposium on Geometry Processing 2012, vol. 27 (2008), No. 1, Aug. 2012, pp. 1735-1744, DOI: 10.1111/j.1467-8659.2012.03178.x.

Xu, Sheng, et al., "Real-Rime MRI-TRUS Fusion for Guidance of Targeted Prostate Biopsies," Computer Aided Surgery, vol. 13, No. 5, Sep. 2008, pp. 255-264, DOI: 10.3109/10929080802364645.

* cited by examiner

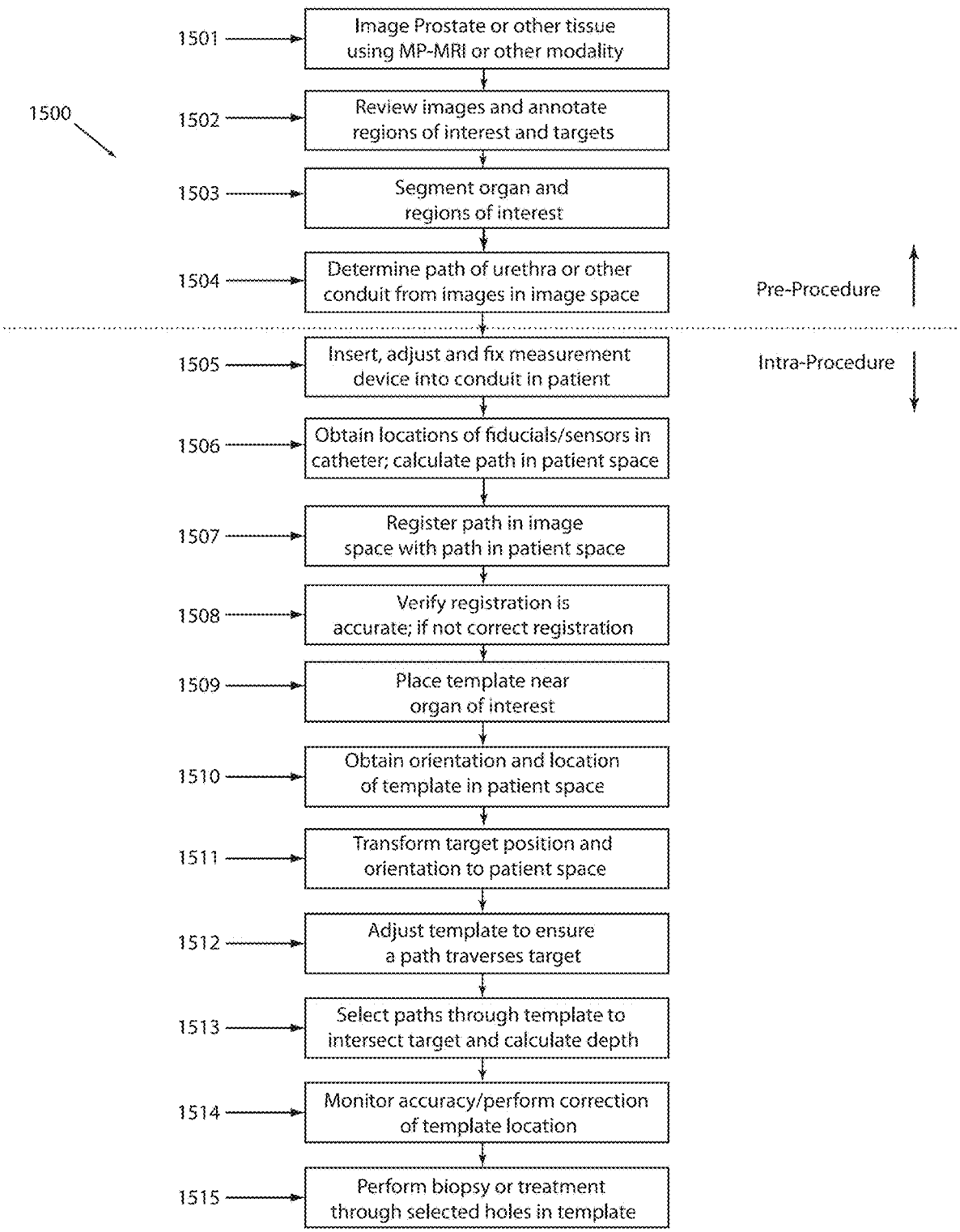

SYSTEMS, METHODS, AND DEVICES FOR REGISTERING AND TRACKING ORGANS DURING INTERVENTIONAL PROCEDURES

CROSS-REFERENCE TO RELATED APPLICATIONS

This application claims the benefit of U.S. Provisional Patent Application Ser. No. 62/842,863, entitled "SYSTEMS, METHODS, AND DEVICES FOR REGISTERING AND TRACKING ORGANS DURING INTERVENTIONAL PROCEDURES", filed May 3, 2019, which is hereby incorporated herein by reference in its entirety.

FIELD OF THE INVENTION

The invention relates to systems, methods, and devices for registering and tracking organs during interventional procedures.

BACKGROUND OF THE INVENTION

Many medical procedures rely on imaging for guidance of procedures, particularly those that are minimally invasive such as needle procedures. Needle and catheter procedures are routinely performed to deliver drugs, take tissue samples, or perform therapy. Diagnostic needle and catheter procedures may include but are not limited to tissue biopsies, optical biopsies, visualization procedures such as endoscopy, interstitial measurement of tissue or systemic properties, ultrasound or measurement of electrical properties of tissue, and/or other diagnostic needle and/or catheter procedures. Therapies may include, but are not limited to, tissue ablation therapies such as radiofrequency ablation, cryoablation, photodynamic therapy, brachytherapy, radiation, laser and microwave ablation; implant of a device such as an artificial heart valve, stent, stent graft, feeding tube, catheter, radioactive seed or electrode; establishment of a channel or pathway such as a shunt; bypass or closure or surgical resection of a portion of tissue; or to place a localization marker or fiducial that can then guide subsequent surgery, radiation therapy, and/or other procedures to the appropriate location. Many other diagnostic procedures and therapies exist that require accurate resection, cutting, and/or sampling, such as, for example, nerve sparing procedures in radical prostatectomy.

When performing these and other interventional procedures, it is important that a physician know the position and orientation of surgical instruments relative to the tissue of interest. While this is sometimes obvious (e.g., direct visualization of an obviously differentiated tissue type), it is often not. Sometimes, diseased or important tissue may look no different than normal surrounding tissue. Sometimes, an instrument's tip position relative to the tissue under investigation may not be directly visualized and occasionally the tissue itself may not be directly visualized. This is especially true for minimally invasive procedures where it is desirable to create as small an entry as possible so structures and tissues of interest may never be visualized.

In many cases, these procedures may be carried out with the assistance of pre- and intra-procedural volumetric imaging such as Computed Tomography (CT), Magnetic Resonance Imaging (MRI), or Positron Emission Tomography (PET). They may also be carried out using optical techniques including visualization through an endoscope, or through the use of some kind of spectroscopy or fluorescence. Two- and three-dimensional ultrasound imaging (US) and X-ray imaging are also used extensively.

In some cases, imaging may be used before an interventional procedure to plan the treatment or diagnostic procedure, or during the interventional procedure itself to help locate the tissue and/or instruments. X-ray, optical imaging, and US are often regarded as real-time or "live" imaging modalities because they may be more portable and convenient than volumetric modalities, and can be easily used during an intervention. In some cases, these imaging devices may not offer as much information as volumetric modalities such as MRI. For example, certain tumors or anatomy that are visible on MRI may not be apparent on US or X-ray, or the quality of the real-time imaging may be insufficient.

Currently, it is challenging to accurately and efficiently target a biopsy or therapy instrument into a target site seen under volumetric methods once a patient has been moved out of the scanner, particularly a CT or MRI scanner. This is because the instrument's location is not seen on the scans once the scans are complete. The same is true for cone beam computed tomography (CBCT) and other modalities where the scanner stops producing images once the scan is complete. While it is possible to perform an intervention in the scanner itself, this may be time consuming, inconvenient, costly, and even dangerous for the patient or physician. Ultimately, while many minimally invasive interventions such as needle procedures do have pre-procedure volumetric imaging available, the procedure itself is performed with the assistance of rudimentary imaging devices such as US or X-ray with the pre-procedure volumetric images available only as static films or on a display workstation uncorrelated to the current patient position.

In some cases, such as those performed under X-ray, the target may not be visible or visible only during injection of contrast and while the X-ray beam is on. This may expose the surgical team and patient to multiple doses of ionizing radiation and the patient to high doses of nephrotoxic contrast agents. Since X-rays offer only two dimensional views a single X-ray image cannot resolve the depth of an object. Accurate instrument targeting requires frequent repositioning of the imager to ensure the instrument is in the correct 3D location.

In some instances, such as those performed using ultrasound (or modifications of US such as Contrast Enhanced Ultrasound (CEUS) or ultrasound elastography), the anatomy may be poorly visualized or presented in a form that makes it difficult for a physician to interpret. Some lesions or anatomy may not be suited to, or visible on ultrasound at all, so it is necessary to "mentally fuse" images from preoperatively-obtained volumetric images with the live ultrasound images.

A physician may also have difficulty identifying a target on the live modality that was previously seen on the pre-operative images especially if they are of different modalities. In some cases, anatomy may look different to or be completely invisible under a live modality.

Additionally, it is often desirable to perform a minimally invasive procedure to minimize chances of severe complications that sometimes accompany surgery. By precisely targeting devices, focal cancer lesions treatments, therapy, or biopsy may be possible without subjecting the patient to a large, invasive procedure that would otherwise be poorly tolerated. Only the diseased tissue may be targeted, and healthy tissue spared.

In some cases, external beams of radiation provide the optimal treatment modality. In these situations, it is important to know where the tissue undergoing treatment is located at all times so that patient motion does not inadvertently cause healthy tissue to be exposed and the tissue undergoing therapy to be undertreated.

In most cases, the location and orientation of an instrument or device must be precisely known in order to optimally treat a patient. For example, the location and orientation of a heart valve delivered by a transapical approach must be known prior to deployment. Other examples include placement of biopsy needles prior to sampling, placement of therapy devices as listed above or devices such as implanted fiducials for marking of tumor boundaries for use in later surgery or radiation therapy. In some cases, needles or other instruments may be inserted to monitor therapy. For example, temperature sensors in the form of needles may be inserted to monitor an ablation procedure. When a plurality of devices are implanted such as needles designed to sample multiple locations or ablate multiple portions of a tumor, it is important to accurately and unambiguously place each in a desired location to ensure the therapy is correctly administered.

Currently, needles and other minimally invasive devices may be directed to targets using techniques that may include freehand placement of needles, image-guided needle procedures, needle guides, template guidance, stereotactic frames, robots, or computer assisted image guided intervention.

Freehand needle procedures may be performed without the use of imaging if the target is large or apparent, such as a palpable lump or nodule. During the technique of freehand needle procedures, needles are typically held in a physician's hand and inserted into the lesion of interest.

Image-guided freehand procedures are similar except that, from time-to-time during the insertion process (or continuously in some cases), an X-ray, CT scan, ultrasound, MRI scan, and/or other imaging technique used to ensure the needle is properly approaching the target and is not impinging on critical structures. This is a very common type of needle procedure. For example, during ultrasound-guided biopsy, an ultrasound transducer may be used to visualize the lesion and path. A needle is then introduced within the scan plane of the transducer so that it can be visualized on its path toward the lesion. This approach may be difficult if the target cannot be easily identified, and may be time consuming or use copious amounts of radiation or contrast agents if X-ray imaging is used.

Another common approach uses "needle guides" that are employed during some ultrasound procedures. In this case, a special guide tube may be attached to an ultrasound transducer. This needle guide is positioned in a known orientation and location relative-to and in the scan plane of the probe, usually by a "snap-on" alignment feature. Once attached to the transducer, the paths of a needle placed into the guidance portion of the needle guide can be predicted along the specific path predefined by the guide. The needle path is displayed on the ultrasound screen as a fixed line, and this path is aligned with the lesion and the needle placed into the target for biopsy, treatment, and/or other procedure. An example of a needle guide may be found in U.S. Pat. No. 8,073,529 to Cermak et al.

Templates are used, for example, in transperineal saturation biopsy. A template "grid" consisting of regularly spaced parallel holes is placed externally adjacent to the perineum of the patient. A transrectal ultrasound may be used to observe the sequential placement of needles through the holes in the grid. Needles are inserted into each hole that covers part of the prostate in succession and a sample of the tissue is taken. Saturation biopsies can be expensive and time-consuming due to the large number of samples (e.g., typically at least sixty, and sometimes twice that number) that are extracted and analyzed. They may also be uncomfortable for the patient.

In some cases, partial or "focal" transperineal biopsies may be performed in which a subset of a saturation biopsy is used to selectively target certain locations within the prostate or tissue being sampled. Based on a scan or other knowledge of the probable location of the cancer (such as the results of a prior biopsy), the suspected area may be preferentially sampled. Even in these reduced biopsies, usually at least 30 biopsy cores are obtained as the technique lacks accuracy.

In a variation, in U.S. Pat. Nos. 9,681,919 and 10,265,137, both of which are hereby incorporated by reference herein in their entirety, systems, methods, and devices are described using custom drilled templates that preferentially targets preselected lesions. In this and the following methods of targeting lesions, the images must be registered to the patient position in order to function correctly.

Various robotically-assisted biopsy techniques are known, using multi-axis robots that serve as a needle aiming and holding devices. Based on volumetric scans, a robot is first registered to a patient. The needle held by the robot is then aligned to the target automatically. A physician delivers the needle to the target either by hand pushing the needle or by directing the robot to do so using an electromechanical control mechanism. External radiation therapy and radiosurgery work in this manner as well, except that the robot directs a beam of radiation to the tumor usually from multiple directions.

Stereotactic biopsy has been used for many years. In this method, a frame is fitted to the patient, typically to the head, in order to obtain needle access to a lesion in the brain. The location of the target relative to the location of the frame is determined from scans and registered. A needle on the frame is aligned to the target using dials and precise scales to move and angle the needle. It is then inserted in a straight path through a trephination or burr hole into the location in the brain.

Various forms of stereotaxy exist, but the technique is currently mainly limited to radiosurgery or radiotherapy using external radiation beams as stereotactic frames, and needles are rarely used any more. The technique is regarded as complex and fairly invasive, and has been largely replaced by computer assisted "frameless stereotaxy."

Frameless stereotaxy or Image-Guided Interventions (IGI) has been enabled by the advent of accurate and inexpensive position sensors. These are able to track the location and orientation of "position indicating elements" that may be attached to the patient and instruments.

IGI systems normally use an externally placed locating device (hereinafter referred to interchangeably as a "tracking system" or a "position sensor"). Position sensors are often specially calibrated camera systems or magnetic field generators although other forms exist. These are used together with an instrument containing one or more trackable components or position indicating elements that can be localized by a locating device or tracking system. Depending on the device and technology, these can, for example, be infrared light emitting diodes (LEDs), reflective spheres, optical fibers, or small electromagnetic sensing coils as position indicating elements.

Position indicating elements are typically attached to instruments such as surgical probes, drills, microscopes, needles, catheters, guidewires, ultrasound transducers, X-ray machines, gantries, and/or other instruments, and to the patient. The spatial coordinates and often the orientation (depending on the technology used) of the position indicating elements can be determined by the tracking system in the coordinate system ("frame of reference") of the position sensor itself. Many tracking systems are able to track multiple position indicating elements simultaneously in the fixed frame of reference of the position sensor. Through geometrical transformations, it is possible to determine the position and orientation of any position indicating element relative to a frame of reference of any other position indicating element tracked by the same tracking system.

As described herein, a variety of different position sensors exist, having different advantages and disadvantages. For example, optical tracking devices may be able to determine the position and orientation of an instrument (equipped with position indicating elements) to a high degree of accuracy. An example of an optical tracking device is the Polaris Vicra (Northern Digital Inc., Waterloo, ON Canada). Optical tracking devices suffer from line-of-site constraints, as they rely on triangulation of a light-emitting diode or reflective marker with several cameras.

An example of an Electromagnetic (EM) tracking device is the Aurora (Northern Digital Inc., Waterloo, ON Canada). EM tracking devices do not require a line-of-sight between the tracking device and the position indicating elements. EM tracking devices may be used with flexible instruments where position indicating elements are placed at the tip of the instruments. They may suffer from electromagnetic interference from metal objects in the vicinity.

A more recently developed position sensor is the optical fiber shape sensing system, such as that disclosed in U.S. Pat. No. 8,811,777 by Younge et al. This device uses an optical fiber position indicating element onto which multiple Bragg gratings (ten to sixty or more) have been deposited that enable the system to determine the shape of an object into which it has been placed in addition to the tip position of the fiber. Each grating acts as an discrete position indicating element.

Another type of position indicating element is a fiducial meant to work with an imaging system. These elements consist of a bead, a capsule, a wire or other element that can be located by an imaging system such as a CT or MR scanner in 3D space. In the case of a wire, multiple "points" along the wire may be identified. A point fiducial such as a bead is capable of acting as a three degree-of-freedom sensor (i.e. spatial position only). Three such fiducials can act as a six degree of freedom sensor (spatial position and rotational orientation) as long as they stay in the same relative position to one another.

Other known position sensors include, but are not limited to, mechanical linkage devices, ultrasonic devices, and global positioning devices. Two or more position sensors of the same or different type may be used simultaneously to expand the tracking volume, or a single position sensor may be calibrated to two or more volumes for optimally measuring position indicating elements in different parts of the tracking volume. When two or more position sensor are used, it may be necessary to either place one at a known and fixed relationship to the other or to track one of the other position sensors with the other (e.g. by securing position indicating elements on the second position sensor) to establish a common frame of reference. In some cases a position sensor may be secured to a movable part of the environment such as a gantry, a procedure table, or part of an imaging system.

Image guided interventions using these systems can be effectively performed if an accurate "registration" is available to mathematically map the position data of position indicating elements expressed in terms of the coordinate system of the tracking device ("patient space") to the coordinate system of the previously imaged data ("image space"). In rigid objects such as the skull or bones, one method of registration may be performed by using a probe equipped with position indicating elements (therefore, the probe itself is tracked by a tracking device) to touch stick-on fiducial markers (such as, for example, small steel balls (x-spots) made by the Beekley Corporation, Bristol, Conn.) placed on the patient prior to imaging. This enables the system to obtain the patient space coordinates of the fiducials. These same fiducials are visible on an image such as, for example, a CT scan and are identified in the image space by indicating them, for example, on a computer display. It is important that the fiducials stay in the same position from the time of the imaging to the time of the intervention, so various steps should be taken to ensure this such as replication of patient position, use of bony landmarks if available, use of permanent fiducials, and/or one or more other appropriate techniques. Fiducials attached to the patient during imaging may be removed and replaced at the time of intervention as long as the fiducial is replaced in the same location. Imaging fiducials do not need to be the same as fiducials used at the time of the intervention as long as they are in the same location.

Once these same markers are co-located in both spaces, a registration transformation or equivalent mathematical construction can be calculated. In one commonly used form, a registration transformation may comprise a 4×4 matrix that embodies the translations, magnification factors and rotations required to bring the markers (and thus the coordinate systems) in one space in to coincidence with the same markers in the other space. Mathematical inversion of the registration matrix, a trivial operation, reverses the direction of transformation.

Two well-known methods for calculating registration matrices include iterative closest points (ICP), described by Gruen and Akca [A. Gruen and D. Akca. Least squares 3d surface and curve matching. ISPRS Journal of Photogrammetry and Remote Sensing, 59:151-174, 2005. DOI: 10.1016/j.isprsjprs.2005.02.006] or singular value decomposition (SVD) may be used to calculate this matrix [Arun, K., HuangSteven, T., BlosteinSteven, D., Blostein, D., Least-squares fitting of two 3-D point sets. IEEE Transactions on Pattern Analysis and Machine Intelligence PAMI-9(5):698-700, 1987. DOI: 10.1109/TPAMI.1987.4767965]. Deformable registration techniques are also possible.

Fiducial markers used for registration may be applied to objects such as bone screws or stick-on markers that are visible to the selected imaging device, or can be implicit, such as unambiguous parts of the patient anatomy. These anatomical fiducials may include unusually shaped bones, osteophytes or other bony prominence, calcifications, features on blood vessels or other natural lumens (such as bifurcations of bronchial airways), individual sulci of the brain, or other markers that can be unambiguously identified in the image and patient. A rigid affine transformation such as the 4×4 matrix described above may require the identification of at least three pairs of non-collinear points in the image space and the patient space. Often, many more points are used and a best-fit may be used to optimize the registration.

Registration for image-guided surgery may be accomplished using different methods. Paired-point registration (described above) is accomplished by a user identifying points in image space and then obtaining the coordinates of the corresponding points in patient space. A version of this, known as "curve registration", is another method of registration that may be performed alone or in combination with paired point registration. Curved structures such as blood vessels may be located image and patient space and registered together to obtain the transformation matrix. Curve registration has an advantage in that if the measurement method provides the local slope of the curve, a better registration may be obtained than by simple matching coordinate points along the curve.

Another type of registration, surface registration, can be done in combination with, or independent of, paired point or curve registration. In surface registration, a cloud of points is obtained in the patient space and matched with a surface model of the same region in image space. A best-fit transformation relating one surface to the other may then be calculated. In another type of registration, repeat-fixation devices may be used that involve a user repeatedly removing and replacing a device in known relation to the patient or image fiducials of the patient.

Some of these registration techniques lend themselves to "automatic" registration requiring minimal user interaction. Automatic registration may, for example, make use of predefined fiducial arrays or "fiducial shapes" that are readily identifiable in image space by a computer. The patient space position and orientation of these arrays may be inferred through the use of a position indicating element fixed to the fiducial array. Other registration methods also exist, including methods that attempt to register non-rigid objects generally through image processing means. These methods are especially fast and convenient for the physician.

Registrations may be performed to calculate transformations between separately acquired images rather than between images and the patient. This may performed by identifying "mutual information" (e.g., the same fiducial markers existing in each image set). In this regard, information visible in one image, but not the other, may be coalesced into a combined image containing information from both.

One such method for doing "image-to-image co-registration" for ultrasound and MRI was presented by Xu et al. in "Real-time MRI-TRUS Fusion for Guidance of Targeted Prostate Biopsies," [Computer Aided Surg., 2008 September; 13(5): 255-264. doi: 10.3109/10929080802364645]. Another method of registration of pre-procedure and intra-procedure images is disclosed in U.S. Pat. No. 9,655,595 to Glossop and Wood entitled "System, Method and Device for Prostate Diagnosis and Intervention," each of which is hereby incorporated by reference herein in its entirety. These methods include the co-registration or matching of two sets of similar but non-identical three dimensional images. The images are not identical even when the same modality is used due to the movement of tissue and the patient between the times of the scans. When the modalities differ (e.g., ultrasound and MRI), the images also differ. Co-registration may take the form of rigid, affine, non-rigid (deformable), and/or other methods, many of which are well known in the art and are a continuous area of research.

Once the images have been co-registered, a mapping (i.e., a transformation matrix) is available that is able to take a point or region on one image set and transfer it to the other image set.

In certain implementations, the location of lesions, targets or regions of interest may be copied or transferred on to other images. For example, if a region or target was detected on MRI, it may be transferred onto CT images, X-ray images, PET images, ultrasound images, or other MRI images, for example. This may be done, for instance, by using the aforementioned transformation matrix to map coordinates from the first image space to the second image space. This "combined image space" may in turn be registered to the patient space using the techniques mentioned above.

Following registration, the two or more spaces are linked through the transformation calculations. Spaces that may be linked may include for example patient and image, image and image, or multiple images and patient. Once registered, the position and orientation of a tracked probe placed anywhere in the registered region may be located on, for example, a scan or set of scans of the region. Likewise, it may be possible to point to a location on one scan and have the matching location be displayed on another scan. Registration is one of the most critical aspects of image guided intervention.

When performing an intervention, a tracking device may be used. Typically the tracking device if used may be connected to a computer system. Scans may also be loaded on to the computer system. The computer system display may take the form of a graphical representation of a probe or an instrument's position superimposed on to preoperative image data. Accordingly, it is possible to obtain information about the object being probed as well as the instrument's position and orientation relative to the object that is not immediately visible to the surgeon. The position and orientation information of the instrument can also be accurately and quantitatively measured enabling the physician to carry out a preoperative plan more accurately.

An additional concept in image-guided intervention is that of "dynamic referencing". Dynamic referencing may account for any bulk or local motion of the anatomy or part thereof relative to a tracking device. This may entail attachment of additional position indicating elements to the anatomy, or other techniques. For example, in cranial surgery, position indicating elements that form the dynamic reference are often attached directly to the head. In prostate surgery, a special Foley catheter may be used to track the prostate with the use of a position indicating element embedded in the catheter (see U.S. Pat. No. 8,948,845 to Glossop et al., entitled "System, Methods, and Instrumentation for Image Guided Prostate Treatment," which is hereby incorporated by reference herein in its entirety). In spine surgery, a dynamic reference attached (via a temporary clamp or screw) to the vertebral body undergoing therapy is used to account for respiratory motion, iatrogenic motion, as well as motion of the tracking device. Dynamic referencing may be used to account for either rigid motion of the tracked anatomy (as in the case of a patient's head or a vertebral body in the spine) or a combination of rigid motion and local deformation such as may occur in soft tissue. In the latter case a model of the tissue is used in combination with position indicating elements to adjust not only the position and orientation of the tissue of interest but also its shape, and therefore the locations of targets within the tissue.

"Gating" may also be used to account for motion of the anatomy. Rather than continually compensating for motion through dynamic referencing, "gated measurements" are measurements that are only accepted at particular instants in time. Gating has been used in, for example, cardiac motion studies. Gating synchronizes a measured movement (e.g., heartbeat, respiration, or other motion) to the start of the measurement in order to eliminate the motion. Measurements are only accepted at specific instants of a repeated motion. For example, gating during image guided intervention of the spine may mean that the position of a tracked instrument may be sampled briefly only during peak inspiration times of a respiratory cycle.

Both registration and use of an image guided intervention system in the presence of anatomical motion is generally regarded as safer and more accurate if a dynamic reference device is attached prior to registration (and/or if gating is used). Instead of reporting the position and orientation of a position indicating element of a tracked instrument in the fixed coordinate system of the tracking device, the position and orientation of the position indicating element of the tracked instrument is reported relative to the dynamic reference's internal coordinate system. Any motion experienced mutually by both the dynamic reference and the tracked instrument is "cancelled out."

With reference to FIG. 1, an organ 101 is depicted (e.g., a prostate gland, kidney, liver, thyroid, or other organ) containing a suspected tumor 102. Tumor 102 may be have been detected by an imaging modality such as MRI, multiparametric MRI, CT, PET, ultrasound, or by some other method. Once detected, it may be desirable to place a needle into tumor 102 for the purposes of biopsy, therapy, or delivering fiducials, for example.

The article by Pinto et al., entitled "Magnetic Resonance Imaging/Ultrasound Fusion Guided Prostate Biopsy Improves Cancer Detection Following Transrectal Ultrasound Biopsy and Correlates with Multiparametric Magnetic Resonance Imaging," The Journal of Urology, Volume 186, Issue 4, 1281-1285. DOI: 10.1016/j.juro.2011.05.078) demonstrates the use of multiparametric MRI in the detection of prostate cancer. Once it is visualized on an imaging modality such as MRI, it may be annotated on the MRI scans. The suspected cancer regions may be marked as single points, as indicated by asterisk (*) point 103. The spatial location, size, and/or orientation may also be modeled or notated and stored in a database or in reference to the images on which it was detected.

In some instances, an organ or region may be segmented or delineated so that its boundaries are apparent. This may assist a physician in understanding the boundaries of the organ. It may further assist in registering the position and orientation of the organ with subsequent images of the organ and, for example, enable it to be projected or fused into images obtained using another imaging modality. For instance, a three-dimensional graphic rendering representing a prostate gland that has been segmented from MRI may be fused with a real-time imaging modality such as ultrasound rather than the actual MRI images to reduce clutter in the live ultrasound images. The organ, in addition to critical structures within or around the organ such as important vessels, nerves, ducts, stones, bones, valves, nodes, and other regions of interest may be segmented.

As shown in FIG. 1, a number of needles 104a, 104b, 104c, and 105 are shown converging onto the tumor, specifically suspected cancer region 103. The needles may be positioned for the purposes of sampling tissue (e.g., for a biopsy) or delivering a treatment as mentioned previously. Both the position and orientation of the needles are important so that while needles 104a, 104b, and 104c may be acceptably placed, needle 105 may transect a structure 106 (e.g., such as the urethra) which may not be acceptable. Using the methods explained above, a physician would attempt to avoid this structure. For example, in a transperineal saturation biopsy of the prostate, a physician may use imaging to constantly monitor for a needle that will violate the urethra.

In an illustrative prior art depiction shown in FIG. 2, a needle 201 is equipped with an electromagnetic tracking sensor or position indicating element 202 that, when connected to a position sensor 203, enables its location and orientation in space to be detected. Position sensor 203 may determine the location of position indicating element 202 in a frame of reference 204 so that a transformation matrix "[T0]" may be reported that determines a translation and rotation to locate position indicating element 202 (and thus the tip of needle 201) in frame of reference 204. Similar devices have been disclosed previously for example in U.S. Pat. No. 6,785,571 to Glossop, entitled "Device and method for registering a position sensor in an anatomical body," which is hereby incorporated by reference herein in its entirety.

A registration step may be performed to relate the position of the actual anatomy 206 in frame of reference 204 with the images 207 of the anatomy. This transformation is indicated as "[T1]" in FIG. 1. This enables a graphic display 209 of the needle on the pre-procedure images 207, which moves around as the needle 201 is moved. Needle 201 may then be placed into the lesions or suspected lesions 210 by observing the graphic display 209 of the needle while manipulating the actual needle 201. When the graphic display 209 of the needle is shown to be in the correct trajectory, needle 201 may be placed into the anatomy 206 and subsequently into lesion 210. There are numerous ways to perform this registration to obtain T1, some of which are referenced above.

In some implementations, an ultrasound, X-ray, or other live imaging modality may be used in conjunction with the pre-procedure images. In one implementation, an ultrasound transducer 211 may be equipped with a position indicating element 212 that indicates the position and orientation of transducer 211 relative to frame of reference 204, indicated here as transformation "T2." If a calibration has been performed, the location and orientation of the scan plane 214 of transducer 211 is known as a fixed transformation "T3." From this, points in the anatomy 206 on the scan plane 214 together with transformations [T1], [T2], and [T3] can yield the location of these points on pre-procedure images 207, and it is possible to fuse the preoperative images with the live images. If the location of needle 201 is known through transformation [T0], it too can be projected on the preoperative and intraoperative images. Note that images from imagine devices must be able to be represented in the patient space of the position sensor (i.e., [T2] is defined) in all references to intraoperative imaging.

Methods of ultrasound calibration to determine [T3] are known in the art, some of which are summarized in the document to Gee et al., entitled "3D Ultrasound Probe Calibration Without A Position Sensor," CUED/FINFENG/TR 488, September 2004 (Cambridge University, Department Of Engineering, Trumpington Street, Cambridge CB2 1PZ, United Kingdom), and in the document to Lindseth et al., entitled "Probe Calibration for Freehand 3-D Ultrasound" (Lindseth F., Tangen G. A., Langø T., Bang J. Ultrasound Med Biol. 2003 November; 29(11):1607-23. DOI: 10.1016/S0301-5629(03)01012-3).

In many cases the registration, gating and dynamic referencing steps can be time consuming and difficult. It is the object of this invention to at least partially overcome these limitations especially in tissues that contain a natural or artificially created conduits.

SUMMARY OF THE INVENTION

The invention addressing these and other drawbacks in the art relates to systems, methods, and devices for assisting or performing guided interventional procedures using conduits within the patient. In various implementations, the systems, methods, and devices described herein assist or perform guided interventional procedures using, for example, radiation, needles, catheters, and/or other instruments, and/or assist in the performance of robotic procedures. In some implementations, the systems, methods, and devices described herein involve new methods for registering soft tissue with pre-procedure scans and/or compensating for tissue motion during the procedure.

According to an aspect of the invention, a system is described that may include a computer device, a tracking device, an imaging device, a template assembly, one or more surgical device or surgical device assemblies, a dynamic reference device, a registration device or other components to assist in guided surgical procedures. The system makes use of a control application on a host computer to generate images of interest for a user.

According to an aspect of the invention, the system may employ templates to assist in guiding instruments to a target. Templates may comprise one or more guide elements that extend through the body of template and may appear as blocks or one or more tubes. They may have integrated or removable position indicating elements or fiducials that enable their pose and location to be established by a position sensor or imaging device.

According to an aspect of the invention, pre-procedure scans of a patient's anatomy may be used to identify targets, including lesions, critical structures, conduits, fiducials, and other aspects of the anatomy. The anatomy may be segmented to provide simplified graphic models of important targets.

According to an aspect of the invention, the geometry of a conduit is discovered by the imaging method. The conduit may be simplified into a skeletonized path that is representative of the complete conduit.

According to an aspect of the invention, a measurement (or measuring) device containing position indicating elements or fiducials may be inserted into a natural or artificially created conduit in a patient and affixed thereto. A registration relating the patient space to image space may be calculated based on the information from the position indicating elements and the geometry of the conduit together with information of the location of the measurement device within the conduit.

According to an aspect of the invention, multiple ways of determining the location of the measurement device in the conduit and performing an initial registration are described.

According to an aspect of the invention, this initial registration may be improved using several described techniques to obtain maximum accuracy of the registration.

According to an aspect of the invention, the measuring device may also be used to dynamically reference the tissue to which it has been affixed and to gate an interventional procedure.

One advantage of the invention is that the systems, methods, and devices described herein facilitate procedures that require the localization of one or more surgical instruments relative to soft tissue anatomy.

An additional advantage of the invention is that the systems, methods, and devices described herein facilitate procedures that may benefit from the rapid simple registration and tracking of the organ of interest.

Yet another advantage of the invention is that the devices described herein may increase accuracy and speed in intervention such as radiation therapy, ablation, or biopsy. Once a measurement device is in place, multiple operations may be performed at once without the need to re-register since the measurement device may include guiding elements or features.

These and other objects, features, characteristics, and advantages of the systems, methods, and devices disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 15 depicts an example flowchart of the operations required to perform interventions such as therapeutic or diagnostic procedures using the techniques described herein, in accordance with one or more implementations of the invention.

DETAILED DESCRIPTION OF THE INVENTION

Described herein are systems, methods, and devices for assisting or performing guided interventional procedures using templates for the purpose of, among other things, marking or annotating regions, providing therapy to a region, sampling an aspect of a region, or cutting or manipulating a region.

Examples of guided interventional procedures may include, but are not limited to, procedures such as surgical resections, biopsies, full or focal ablation of a tumor or tissue, injection of an agent such as a drug, placement of fiducials, placement of brachytherapy seeds, directing a radiation beam, marking or resection of the skin in preparation for a surgical procedure, marking or resection of an aspect of anatomy that is either a target or a critical location that must be avoided, placing monitoring sensors such as temperature sensors, placing stabilizing instruments, placement of devices such as stents or stent grafts, and placement of cardiac valves or other such devices. Guided interventional procedures may also include marking and manipulation of tissues or fragments thereof.

Guided interventional procedures may further make use of therapeutic devices such as, for example, needles, ablation needles, radiofrequency ablation needles, lasers and laser delivery systems, blades, cryoablation needles, microwave ablation needles, irreversible electroporation (IRE) probes, HIFU delivery systems, cutting devices such as scalpels or electrocautery devices, and radiation delivery devices, as well as various other therapeutic devices. Such procedures may also make use of monitoring probes for measuring temperature or dose. Such procedures may further make use of probes that perform a protective function such as cooling an area that is adjacent to a region that is being ablated using heat.

Example System Configuration

Figure 3:
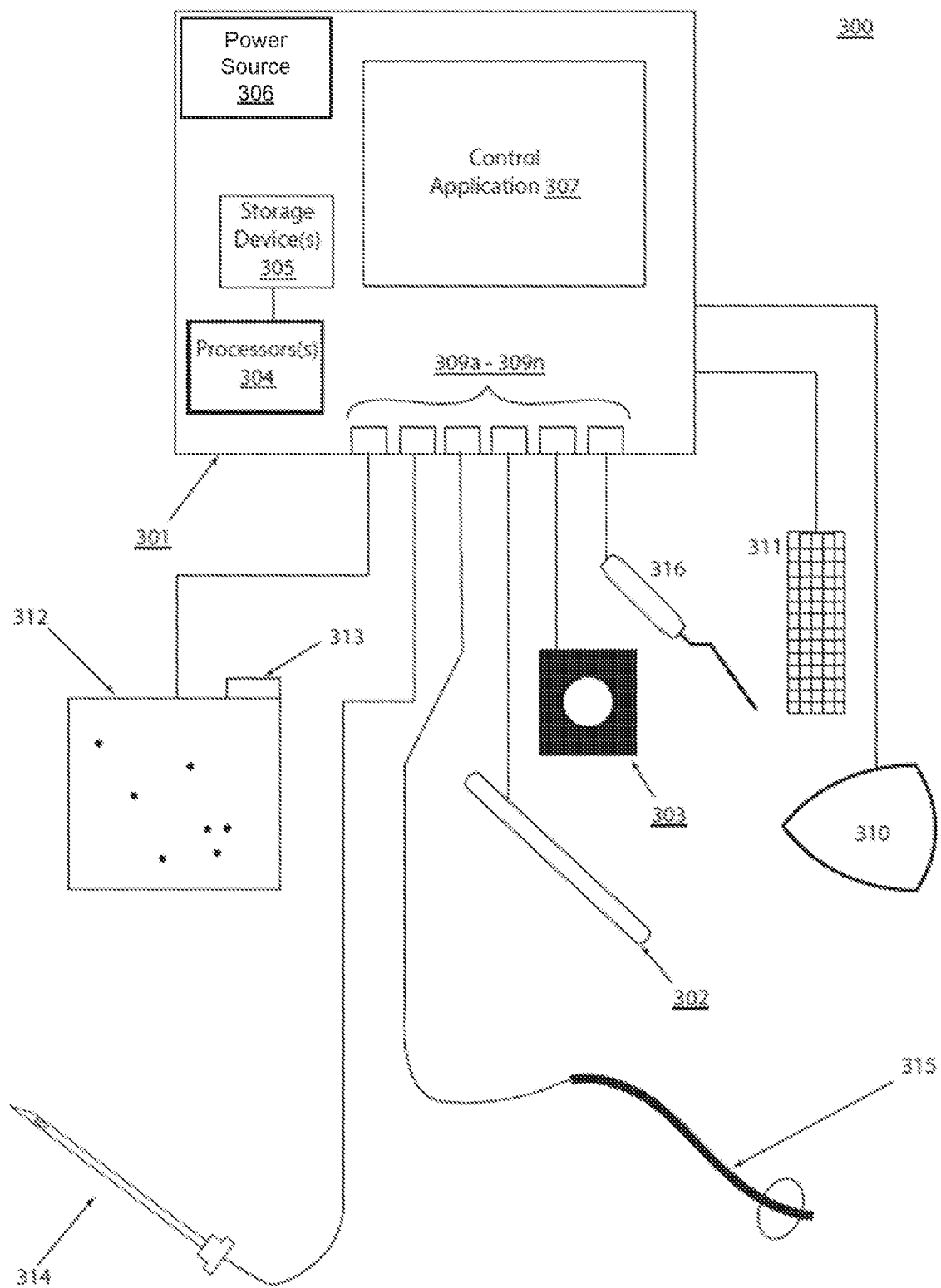
FIG. 3 is a schematic view of an example system for assisting or performing guided interventional procedures, in accordance with one or more implementations of the invention.

FIG. 3 is a schematic view of an example (and non-limiting) system 300 for assisting or performing guided interventional procedures using templates, in accordance with one or more implementations of the invention. System 300 may include a computer device 301, a tracking device 302, an imaging device 303, a template assembly 312, one or more surgical device or surgical device assemblies 314, a dynamic reference device 315, a registration device 316, and/or other components.

Computer Device 301

Computer device 301 may be or include one or more servers, personal computers, portable (e.g., laptop) computers, mobile computers, tablet computers, cell phones, smart phones, PDAs, or other computer devices. Computer device 301 may send, receive, store, or manipulate data necessary to perform any of the processes, calculations, image formatting, image display, or other processing operations described herein. Computer device 301 may also perform any processes, calculations, or processing operations necessary for the function of the devices, instruments, or other system components described herein.

Computer device 301 may include one or more processor(s) 304, one or more storage device(s) 305, a power source 306, a control application 307 comprising computer program instructions, one or more inputs/outputs 309a-309n, at least one display device 310, one or more user input devices 311, or other components.

Processor(s) 304 may include one or more physical processors that are programmed by computer program instructions that enable various features and functionality described herein. For example, processor(s) 304 may be programmed by control application 307 (described below) and/or other instructions.

Computer 301 may be connected to other computer devices and/or other system components via a network or one or more wired or wireless connections to connect to the Internet, an intranet, another computer, a server, a client, a host, a virtualization platform, a PAN (Personal Area Network), a LAN (Local Area Network), a WAN (Wide Area Network), a SAN (Storage Area Network), a MAN (Metropolitan Area Network), a data center, or other computer resources.

Storage device 305 may comprise random access memory (RAM), read only memory (ROM), and/or other memory. The storage device may store the computer program instructions to be executed by processor(s) 304 as well as data that may be manipulated by processor(s) 304. Storage device 305 may also comprise floppy disks, hard disks, USB drives, solid state drives (SSD), optical disks, tapes, or other storage media for storing computer-executable instructions and/or data. Storage devices may also include cloud storage or off-site storage on a remote server or database.

Display device 310 may comprise a computer monitor or other visual display device such as, for example, an LCD display, an LED LCD display, an OLED display, a plasma screen display, a cathode ray tube display, or other display device.

Input device 311 may comprise a mouse, a stylus, a keyboard, a touchscreen interface (which may be associated or integrated with display device 310), a voice-activated input device (e.g., including a microphone and/or associated voice processing software), or other device that enables a user (e.g., a physician performing a procedure, an assistant thereto, or other user) to provide input to computer device 301 and/or other components of system 300. One or more input devices 311 may be utilized. In one implementation, display device 310 and input device 311 may together be configured as a mobile computing platform such as a tablet computer that is connected wirelessly to computer 301. Other configurations may be implemented.

Inputs/outputs 309a-309n enable various system components such as tracking device 302, imaging device 303, template assembly 312, one or more surgical device or surgical device assemblies 314, dynamic reference device 315, a registration device 316, and/or other components to communicate with computer device 301 (e.g., in a wired or wireless manner) as known and understood by those having skill in the art.

Computer device 301 may further be operatively connected (e.g., via the aforementioned network) to one or more databases. A database may be, include, or interface to, for example, an Oracle™ relational database sold commercially by Oracle Corporation. Other databases, such as Informix™, DB2 (Database 2) or other data storage, including file-based, or query formats, platforms, or resources such as OLAP (On Line Analytical Processing), SQL (Structured Query Language), a SAN, Microsoft Access™ or others may also be used, incorporated, or accessed. The database may comprise one or more such databases that reside in one or more physical devices and in one or more physical locations. The database may store a plurality of types of data and/or files and associated data or file descriptions, administrative information, or any other data, as described herein.

Tracking Device 302

In some implementations, tracking device 302 may be used. Tracking device 302 may comprise, for example, an electromagnetic tracker, an optical tracker, a GPS tracker, an acoustic tracker, a fiber optic tracker, a capacitive, a mechanical tracking system, or other tracking device.

Imaging Device 303

Imaging device 303 may include X-ray equipment, computerized tomography equipment, positron emission tomography equipment, magnetic resonance imaging equipment, fluoroscopy equipment, ultrasound equipment, an isocentric fluoroscopic device, a rotational fluoroscopic reconstruction system (e.g., CBCT), a multi-slice computerized tomography device, an intravascular ultrasound imager, an optical coherence tomography (OCT) device, an optical imaging device, a single photon emission computed tomography device, a magnetic particle imaging device, or other imaging/scanning equipment.

Figure 1:
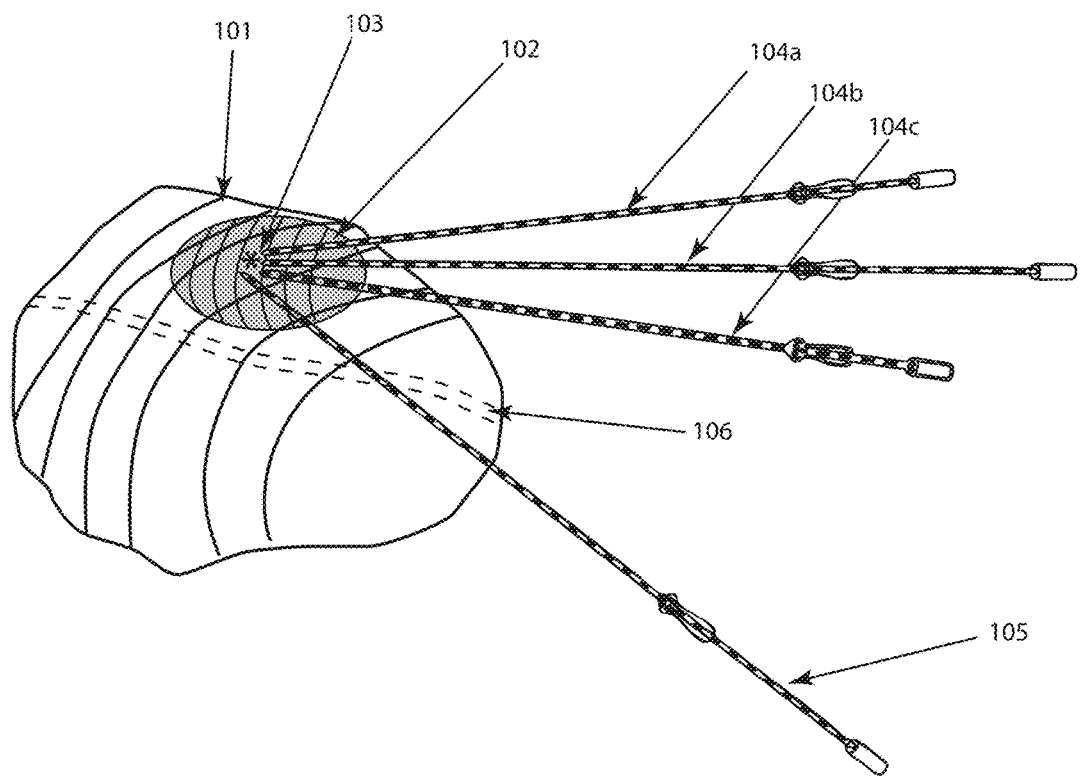
FIG. 1 depicts needles targeted toward a suspected lesion in an organ, including a needle that traverses a sensitive structure.
Figure 2:
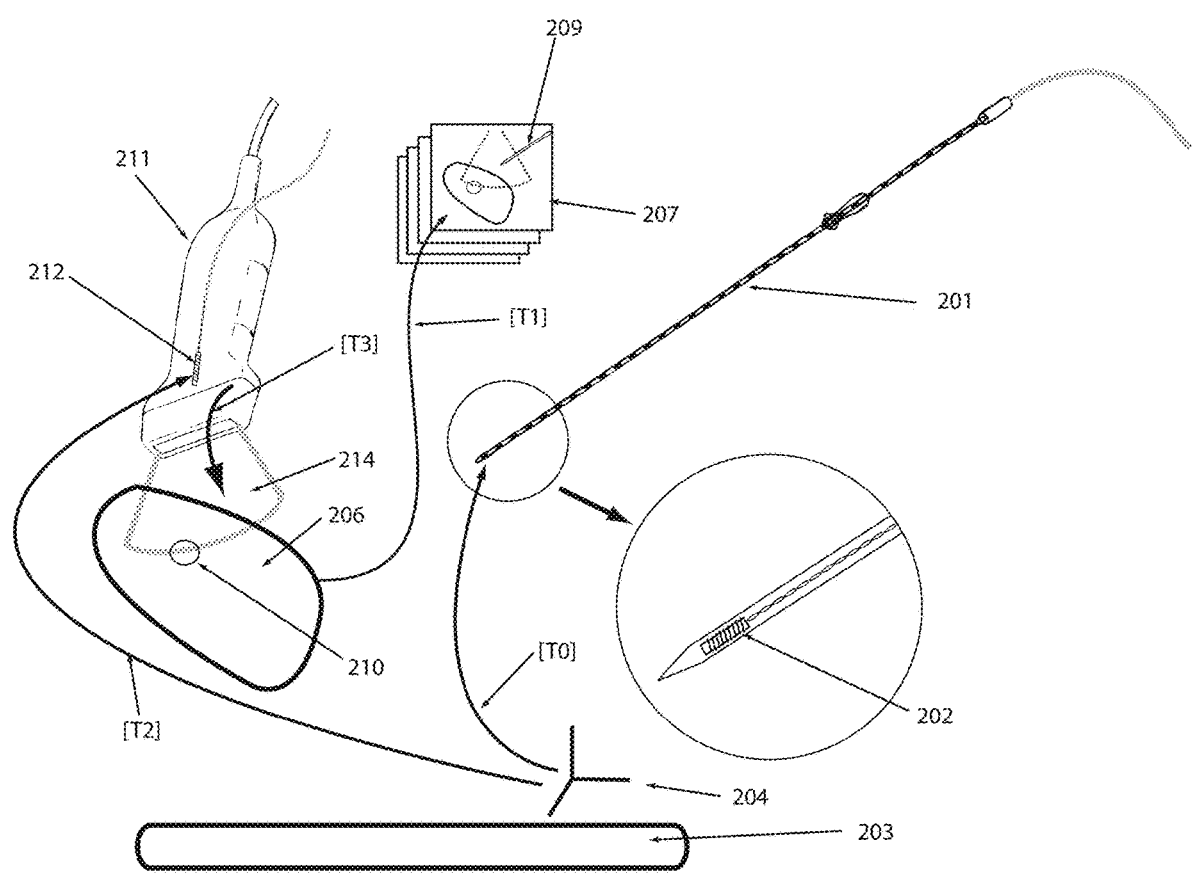
FIG. 2 illustrates a prior art system in which an ultrasound equipped with position indicating elements is used together with a needle containing a position indicating element to place a needle in a patient's anatomy.

In some implementations, imaging device 303 may include one or more devices so that its location and orientation may be tracked by tracking device 302. For example, an ultrasound device may include a position-indicating element enabling its scan plane to be known as shown in FIG. 2. Similarly, a fluoroscope may include a tracking target such as that described in U.S. Pat. No. 8,046,052 to Verard et al., and illustrated in U.S. Design Pat. No. D466,609 to Glossop, each of which is hereby incorporated herein by reference in their entirety.

Template Assembly 312

According to an aspect of the invention, template assembly 312 may comprise a template (also referred to as a targeting template or guide) and a position-indicating element or template tracker 313, which may be attached (permanently or removably) to the template or to a frame that surrounds (or encompasses) all or a portion of the template.

Template tracker 313 may comprise a mechanical encoder, or an optical, electromagnetic, optical fiber, and/or other tracker (described in greater detail below) that can be tracked by tracking device 302.

Further, although not illustrated in FIG. 3, the template assembly may further comprise a support mechanism or structure used to support and/or position the template assembly vis-à-vis a target (e.g., a patient's anatomy). The support mechanism may comprise dials or other controls to adjust and fine tune the position of the template. Examples of a support mechanism may include a Biojet (D&K Technologies GmbH, Barum Germany) or the Multi-purpose Workstation LP (Civco Inc., Coralville, Iowa) that may include motors and/or encoders. In one implementation, the template assembly may be supported and/or moved into position in an automated manner using a robotic mechanism attached to the support mechanism. In an implementation, the template assembly may be the gantry of an external beam radiotherapy (EBRT) machine or HIFU system.

Surgical Devices or Device Assemblies 314

In some implementations, system 300 may include one or more surgical devices or device assemblies 314, the position and orientation of which may be tracked by tracking device 302 or be untracked and used together with template 312. Examples of surgical devices may include therapeutic devices such as needles, ablation needles, radiofrequency ablation needles, lasers and laser delivery systems, blades, electrocautery devices, cryoablation needles, microwave ablation needles, HIFU delivery systems, radiation delivery devices, and/or other therapeutic devices. Monitoring probes for measuring temperature or dose, etc. may also be used along with probes that perform a protective function such as displacing, immobilizing, and/or cooling an area that is adjacent to a region that is being ablated using heat. In some implementations, needles may further serve as elements that also restrain the anatomy from motion.

Dynamic Reference Device 315

In one implementation, system 300 may include a dynamic reference device 315 capable of tracking a patient's anatomy. Examples of dynamic reference device 315 may include, but are not limited to, a tracked Foley catheter, a multi-function device (e.g., as described in U.S. Pat. No. 7,751,868 to Glossop, which is hereby incorporated by reference herein in its entirety), a tracked needle, a K-wire (e.g., as described in U.S. Pat. No. 7,840,254 to Glossop which is hereby incorporated by reference herein in its entirety), and/or other type of dynamic reference device.

Registration Device 316

In an implementation, system 300 may include a registration device 316, such as a probe, a catheter, fiducials, a tracked ultrasound, a multifunction device (such as described in U.S. Pat. No. 7,751,868), and/or other type of registration device.

Control Application 307

As previously noted, computer device 301 may host control application 307. Control application 307 may comprise a computer software application that includes instructions that program processor(s) 304 (and therefore computer device 301) to perform various processing operations.

In one implementation of the invention, control application 307 may cause computer device 301 to send, receive, and/or manipulate data regarding the anatomy of a patient, one or more objects, or other data. This data may be stored in memory device 305, or in another data storage location (e.g., the one or more databases described above). In some implementations, computer device 301 may receive live data (in real-time), or stored data. Computer device 301 may send, receive, and/or manipulate data regarding the location, position, orientation, or coordinate(s) of a position indicating element (e.g., sensor coils or other position indicating elements), or one or more other elements, received by tracking device 302. This data may also be stored in memory device 305 or in another data storage location (e.g., the one or more databases described above).

Control application 307 may further cause computer device 301 to produce, format, reformat, or otherwise manipulate one or more images, position/orientation/location data, or other data. Images may be displayed on display device 310. In some implementations, one or more live images may be displayed. Display device 310 may further display (or otherwise convey) audio data in addition to, or instead of, visual data. Such an audio display may produce tones or other indicators regarding the system.

Control application 307 may additionally cause computer device 301 to generate and display images of the anatomy of a patient along with the position or orientation of an instrument, fiducials, or both (or other information) superimposed thereon in real-time such that motion of the tracked instrument within the anatomy of the patient is indicated on the superimposed images for use in an image-guided procedure.

In some implementations, indicators (e.g., markings, lines, circles, spheres, letters, numbers or other indicators) may be produced on an image of the anatomy of a patient. These indicators may mark or identify features such as the boundaries of another image stored in memory device 305.

In some implementations, control application 307 may facilitate mapping of a target lesion (e.g., a cancerous region) or other portion of a patient's anatomy, or other operations related to a map of the target lesion or portion of the patient's anatomy. For example, control application 307 may generate and display (e.g., on display device 310) the position of a targeting template relative to a location in a target lesion, a projected path (of the target paths of the targeting template) including a path a needle or other instrument inserted into a hole of the targeting template will follow if the needle or instrument is extended past a distal end portion of the template. Control application 307 may additionally generate and display (e.g., on display device 310) a point at which a needle or other instrument placed in a hole of the template will intersect a target lesion if the projected path of the needle or instrument intersects the determined path of the target lesion, as well as an indicator of the closest approach from a needle or other instrument passing through a hole in the template to the target lesion if the projected path of the needle or instrument does not intersect tissue not intended to be treated or biopsied. Additional displays may be presented.

The foregoing system architecture is an example only, and should not be viewed as limiting. The invention described herein may work with various system configurations. Accordingly, more or less of the aforementioned system components may be used and/or combined in various implementations. For example, in FIG. 3, as well as in other drawing Figures, different numbers of entities than those depicted may be used.

Templates

Figure 4:
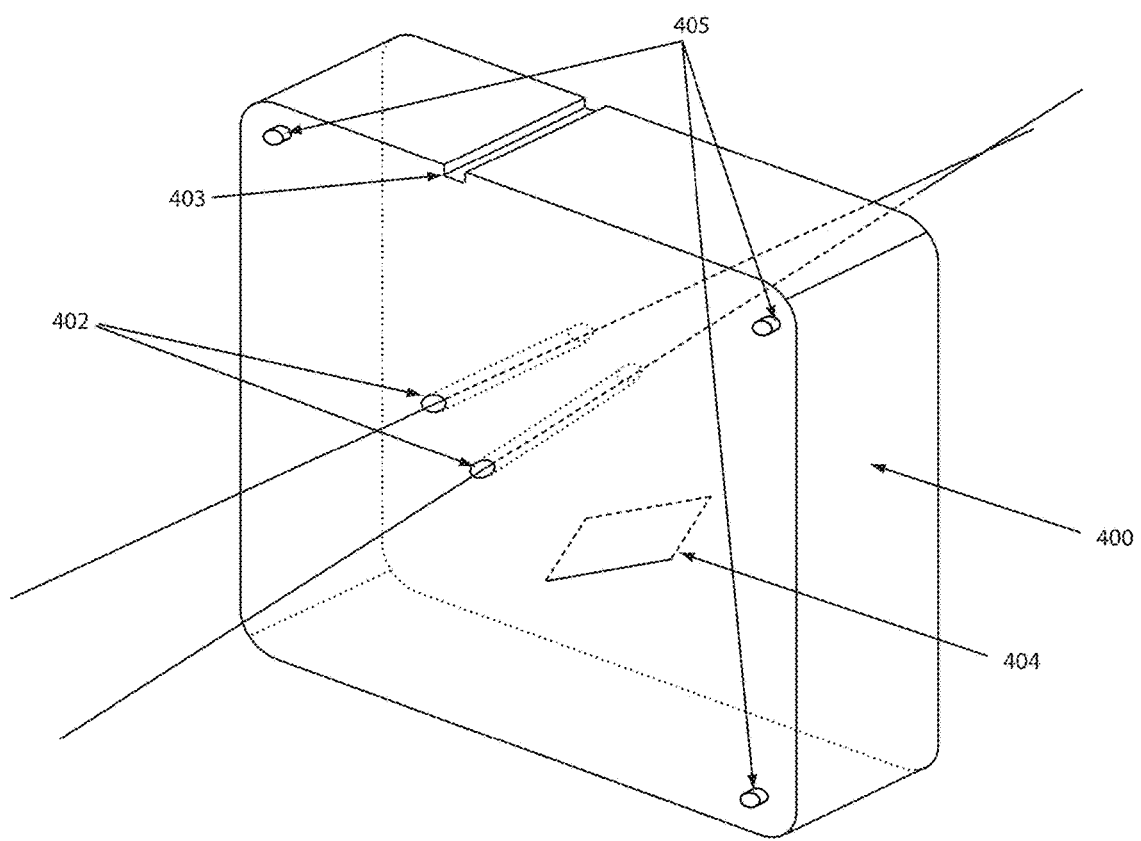
FIG. 4 is an example schematic representation of a template, in accordance with one or more implementations of the invention.

FIG. 4 is an example depiction of a template 400 (which may also be referred to interchangeably herein as a "targeting template" or "guide"), in accordance with one or more implementations of the invention.

In one implementation, template 400 may comprise a solid block of biocompatible material such as, for example, glass, stainless steel, titanium, plastics such as polycarbonate, Delrin, polyethylene, polyetheretherketone (PEEK), ethylene vinyl acetate, polyphenylsulfone (PPSU), polysulfone (PSU), acrylonitrile butadiene styrene (ABS), or other material. In some implementations, template 401 need not comprise a biocompatible material if it is suitably draped (or otherwise covered) in a sterile barrier material. Although depicted as a square in FIG. 4, template 400 may have any shape. Template 400 may also comprise a curved or contoured structure. Template 400 may also be composed of two or more sheets separated by a spacer. For example, template 400 may be composed of two or more sheets separated by a spacer, as described in U.S. Pat. No. 10,265,137, which is hereby incorporated by reference in its entirety.

As shown in FIG. 4, template 400 may comprise one or more guide elements 402 that extend through the body of template 400. For ease of explanation, a guide element 402 may be referred to throughout this detailed description as a "hole." It should be appreciated, however, that other similar descriptors may be used in lieu of "guide element" including, but not limited to, a trajectory, passage, lumen, or channel. Further, as used herein, a pair of holes (or openings) may be described as defining an instrument trajectory or channel. For example, a first channel that enables passage of a first medical device through a body of template 400 may be defined by a first channel opening (or entrance or hole) on a first side of the template body and a corresponding first channel opening (or exit or hole) on a second side of the body of template 400. Likewise, a second channel that enables passage of a second medical device through the body of template 400 may be defined by a second channel opening (or entrance or hole) on the first side of the template body and a corresponding second channel opening (or exit or hole) on the second side of the body of template 400, and so on. In some implementations, template 400 may have multiple channels for enabling passage of multiple medical devices through the template body.

In some implementations, a template may be custom made for each procedure or pre-formed. Pre-formed template holes may be arranged in a rectangular grid, a concentric series of circles, a single or group of tubes, and/or other configuration. Predrilled holes may be of different diameters. Holes in the template grid may also be labelled so that it is possible to uniquely address an individual hole using these labels to describe them. For example, in a rectangular grid, rows might be labelled by numbers and columns by letters so that the combination of a letter and number will correspond to a particular hole.

In some implementations, one or more of holes 402 may be used for different purposes. For example, some holes may comprise defined instrument trajectories, such that needle-like instruments passing through template 400 would follow the trajectory of the holes 402. Some holes may be used for therapy devices, such as thermal ablation instruments, while adjacent holes may be used for placing devices for monitoring temperature (such as thermocouples), or even warming or cooling devices to protect sensitive tissue from thermal damage. Still other holes may be used to inject therapeutic agents and/or other compounds or articles. Although described and illustrated as holes for ease of reference, trajectories (or passages or channels) 402 may have any cross-section (e.g., linear shapes such as 404 allowing passage of blades or other planar instruments).

One or more holes 402 may be placed into template 400 at various orientations. In one implementation, the holes 402 may be created using a Computer Numerical Control (CNC) drilling or milling machine. Alternatively, the holes may be made using electrical discharge machining or any other type of technology designed to bore or create holes. In one implementation, template 400 and holes 402 may be created using an additive technology such as a three-dimensional (3D) printing system of which multiple technologies exist.

In an implementation, template 400 may further comprise one or more locating features 403 such as channels, divots, holes, and/or other types of locating features. Locating features 403 may be used to position template 400, or assist in mounting items to template 400. Registration features such as fiducial features 405 may also be present.

Figure 5:
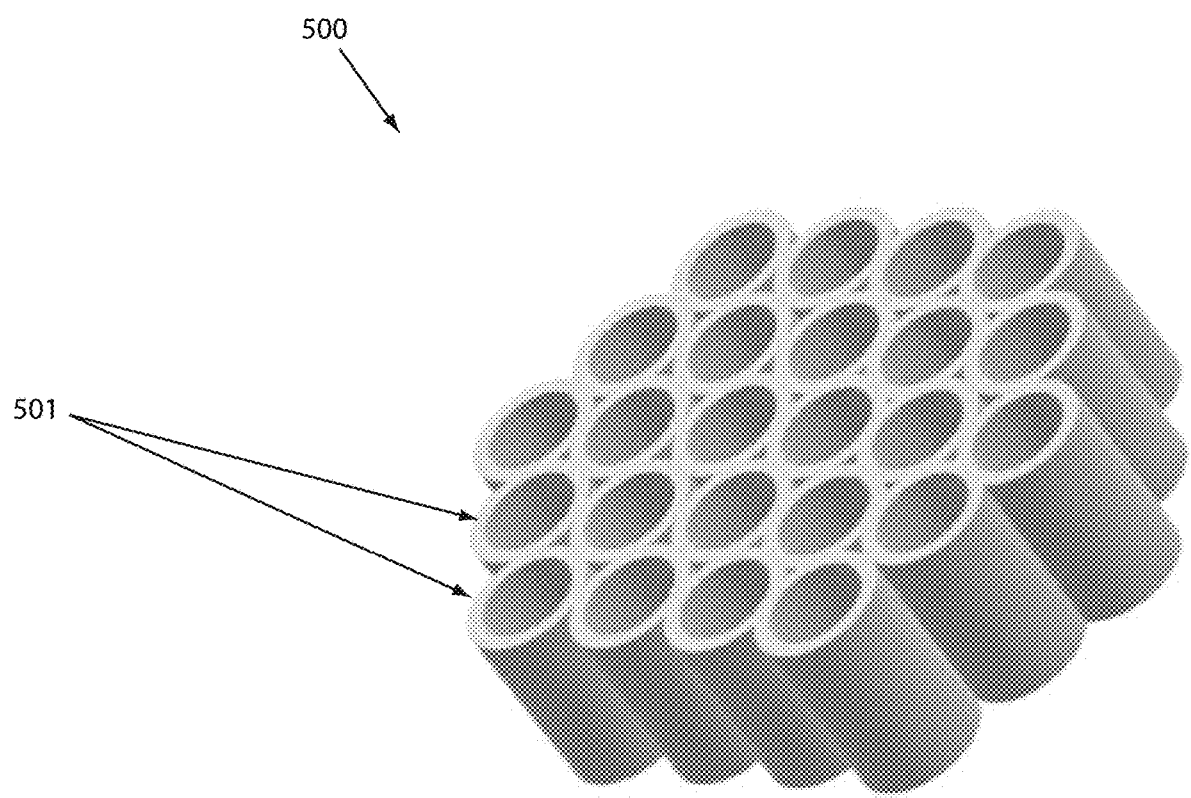
FIG. 5 is an example schematic representation of a template composed of tubes, in accordance with one or more implementations of the invention.

Template 400 may also be constructed as indicated in FIG. 5 (i.e., as groups of tubes joined together 501) in which the holes are the lumens of the tubes together forming a template here depicted as item 500. In a simpler form, a template consisting of a single tube may be used to allow passage of instruments to the target.

Figure 6:
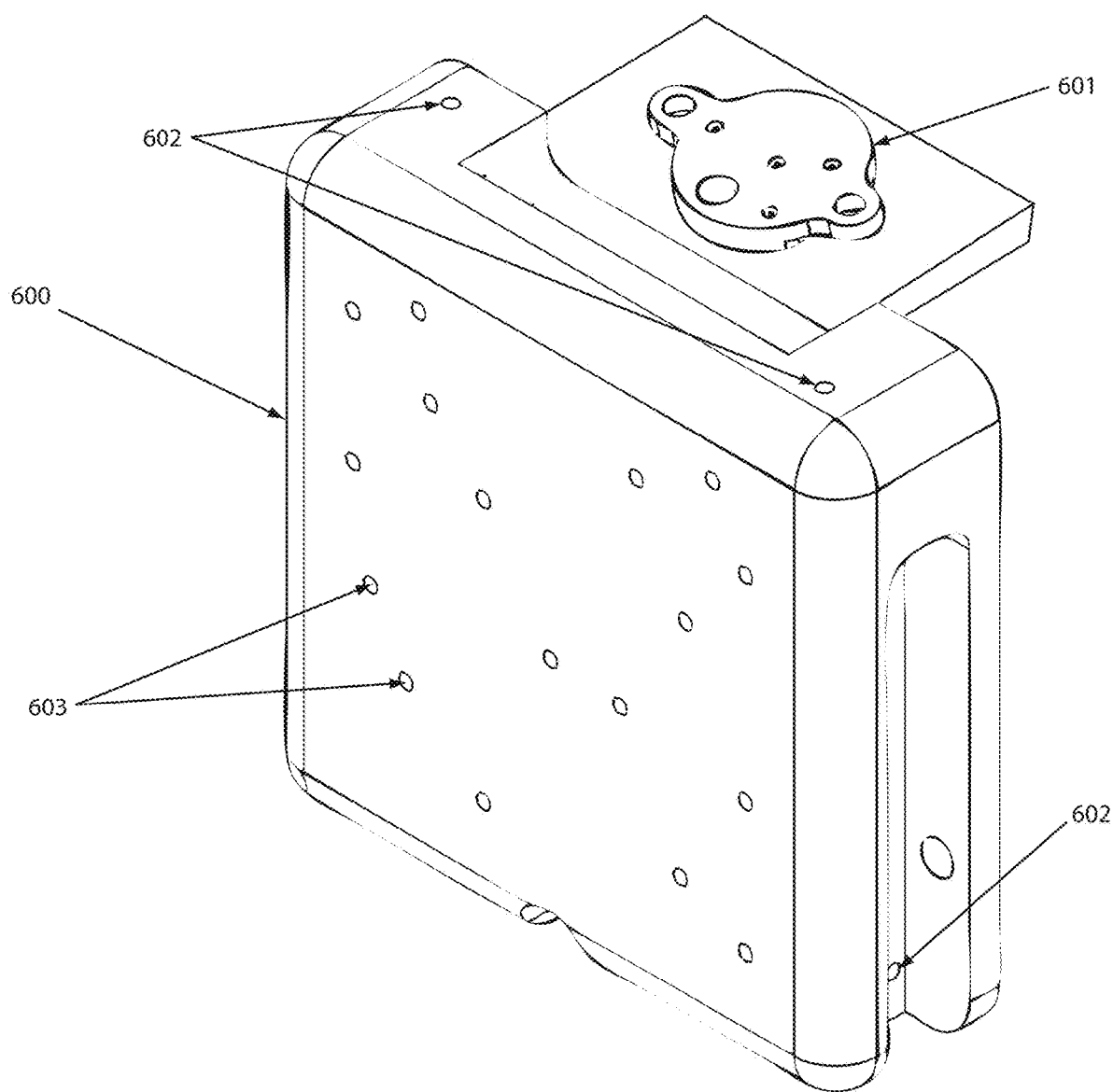
FIG. 6 is a schematic representation of a template with a position indicating element and fiducials attached, in accordance with one or more implementations of the invention.

FIG. 6 is a schematic representation of a template 600 with a position-indicating element 601 and one or more fiducial features 602 attached, in accordance with one or more implementations of the invention. Position-indicating element 601 may be permanently affixed to (or integrated into) template 600. Alternatively, position-indicating element 601 may be removable and replaceable in the same position on template 600. Further, position-indicating element 601 may be permanently affixed (or releasably coupled) to a frame assembly that surrounds (or encompasses) all or a portion of template 600. In various implementations, the location and orientation of instrument passages 603 are known relative to position indicating element 601, such that when position indicating element 601 is located using the position sensor, so too are instrument passages 603.

Figure 7:
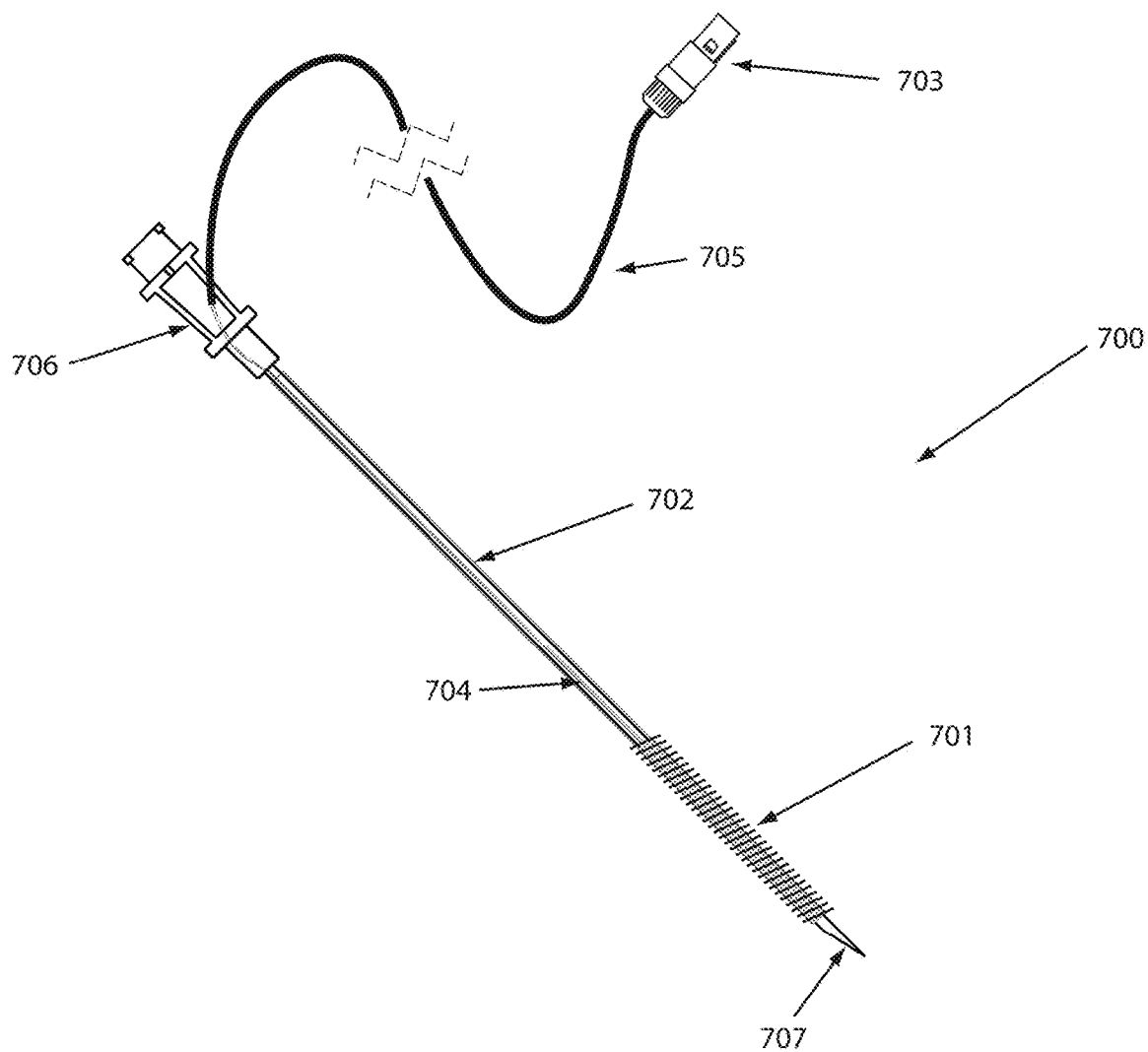
FIG. 7 is an example depiction of a template composed of a single tracked needle, in accordance with one or more implementations of the invention.

In an implementation shown in FIG. 7, a template in the form of one or more tubes may be equipped with an attached position indicating element such as an LED array, electromagnetic sensor or FBG sensor. This enables the position indicating element to help locate the entry point and orientation of the one or more tubes. FIG. 2 showed a position indicating element 202 embedded within a tube. FIG. 7 depicts a schematic representation of a template composed of a single tube with an integrated position indicating element exterior to the tube further illustrating the concept of tube tracking. Here, the tracker is a coil winding 701 around the outside of tube 702 capable of being tracked by an electromagnetic position sensing system. The coil winding 701 may be connected to plug 703 by lead-wires 704 and cable 705. Template 700 (a "tracked cannula") may contain a hub 706 attached to tube 702. It may include a sharp tip 707 so that it may be introduced through tissue.

Tube 702 may contain one or more layers of insulation to prevent shorting and to ensure that surfaces touching the patient are biocompatible and to provide electrical resistance. Layers may include polymers such as polyimide, PTFE (polytetrafluoroethylene), polyester, FEP (Fluorinated Ethylene Propylene), silicone, poly (p-xylylene) polymers, PEEK (Polyetheretherketone), Acrylated Olefin, Tygon, and/or other polymers. Several types and layers of insulation materials may be used in a single device.

In addition, tube 702 itself may be manufactured from a grade of stainless steel, titanium, plastic, or other material that is compatible with the position indicating element, the precise application, and other aspects critical to it use and environment of use. If the tracked cannula contains a tracking attachment, it may be integrated or removable, reusable or single use.

In an implementation, tube templates may be positioned by removably placing a stylette needle containing a sensor (such as item 202 that was described with reference to FIG. 2) into one or more cannulas. While the tracked stylette is within the cannula it may assist in the placement of the cannula, after which it may be withdrawn to allow a separate instrument to be inserted through the cannula.

In an embodiment, tube 702 may contain multiple sensors such as coils or gratings along its length so that the shape of the tube may be determined.

Tube 702 may be rigid or flexible such as a catheter and contain multiple lumens for various purposes.

The one or more templates 700 may be placed using a robotic mechanism, a stereotactic mechanism, and/or other mechanism. In an implementation, the tubes may be held in place by a support mechanism (not pictured).

Use of Template in a Guided Interventional Procedure

Figure 8:
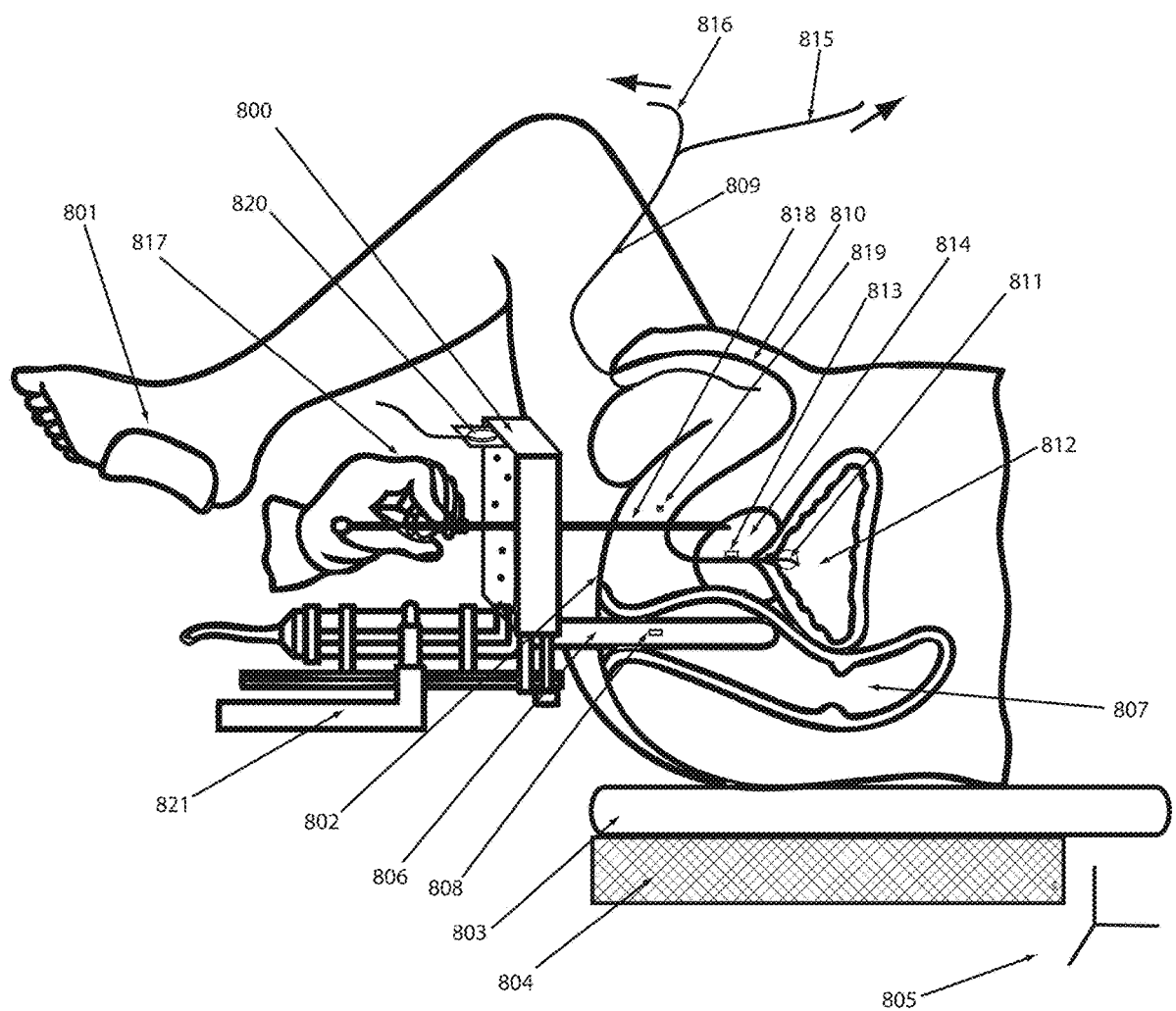
FIG. 8 is an example depiction of a guided interventional procedure, in accordance with one or more implementations of the invention.

FIG. 8 is an example depiction of a template 800 used in a guided interventional procedure (in this case, a needle procedure), in accordance with one or more implementations of the invention. In particular, FIG. 8 depicts a patient lying on an operating table 803 undergoing a procedure. The patient is shown in a lithotomy position with feet resting in stirrups 801 with the patient's perineum 802 positioned near the front of operating table 803. A position sensor 804 (such as, for example, an electromagnetic field generator or optical camera array) is positioned near the patient. A coordinate system 805 is associated with position sensor 804. In this example, and non-limiting implementation, a TRUS probe 806 is placed in the patient's rectum 807 to assist in visualizing the prostate. TRUS probe 806 may incorporate a removable or permanent position indicating element 808 so that the location and orientation of the probe's scan plane is known assuming a calibration as indicated previously has been performed. A transperineal ultrasound probe could be used as well.

In this example, a Foley catheter 809 may be inserted into the urethra 810. At the distal end of catheter 809, a balloon 811 may be inflated to secure the catheter at the neck of the bladder 812. On or in catheter 809, position indicating elements or fiducials denoted here as 813 may be positioned in the vicinity of the prostate gland 814. Wire(s) or fibers 815 from position indicating element 813 may be connected to the position sensor 804. Wire 815 may not be needed in the case where 813 are passive fiducials. The lumen 816 of catheter 809 may be used to drain urine from the bladder.

During a guided interventional procedure, a physician (depicted here by gloved hand 817) may use one or more instruments 818 that may optionally include a position indicating element to assist in positioning instrument 818 in a specific location in prostate 814 by directly piercing the perineum 802. In an implementation, instrument 818 may comprise a biopsy needle, hollow cannula, therapy needle such as a laser, or other device. In an implementation, instrument 818 may comprise a standard instrument that may or may not include a position indicating element. In one or more implementation, one or more "check fiducials" 819 may be applied to the patient. In some implementations, check fiducials 819 may include position indicating elements. In some embodiments, natural fiducials such as bones, calcifications, etc. may be designated as check fiducials.

According to an aspect of the invention, template 800 may be positioned at a predetermined distance and/or angle from perineum 802. A position indicating element 820 (similar to position-indicating element or tracker 602 of FIG. 6) may be fixed to template 800 such that it is able to track the location and orientation of template 800 with respect to frame of reference 805. In one implementation, if template 800 cannot be placed in the correct location due to interference with the patient and/or equipment, another template (if available) that was created for placement in a different assumed location may be utilized. One or more instruments 818 may be inserted through one or more holes of template 800 to a predetermined depth and into prostate 814, according to a pre-procedure plan.

In an implementation, TRUS probe 806 (or other ultrasound probe) may be affixed to a support mechanism 821. Support mechanism 821 may comprise device such as a Biojet (D&K Technologies GmbH, Barum Germany) or the Multi-purpose Workstation LP (Civco Inc., Coralville, Iowa) that may include motors and/or encoders to help position TRUS probe 806 in the patient. Ultrasound probe 806 may be held freehand and/or not otherwise attached to the support mechanism 821.

In an implementation, support mechanism 821 may also hold template 800 (or a frame assembly that surrounds (or encompasses) all or a portion of template 800. In an implementation, template 800 may be moved independently from TRUS probe 806. Encoders on support mechanism 821 may report the relative location of the template 800. The position and orientation of TRUS probe 806 may be tracked using encoders on support mechanism 821. In these instances, it may not be necessary to include position indicating elements (e.g., such as TRUS probe position indicating element 808 and template position indicating element 820). In such instances, position sensor 804 may be optional unless another position indicating element (e.g., such as catheter position indicating element 813) is used.

In one implementation, template 800 may be moved into position using dials or other controls on support mechanism 821. In an implementation, template 800 may be moved into position in an automated manner using a robotic mechanism (such as a gantry) attached to support mechanism 821. In an implementation, TRUS probe 806 may be moved in a similar way.

In an implementation, the template could be used to guide needles through a transrectal approach instead of transperineal as described here. The template in this case be attached to the ultrasound probe reducing the need for an additional template tracker.

Catheter

Figure 9:
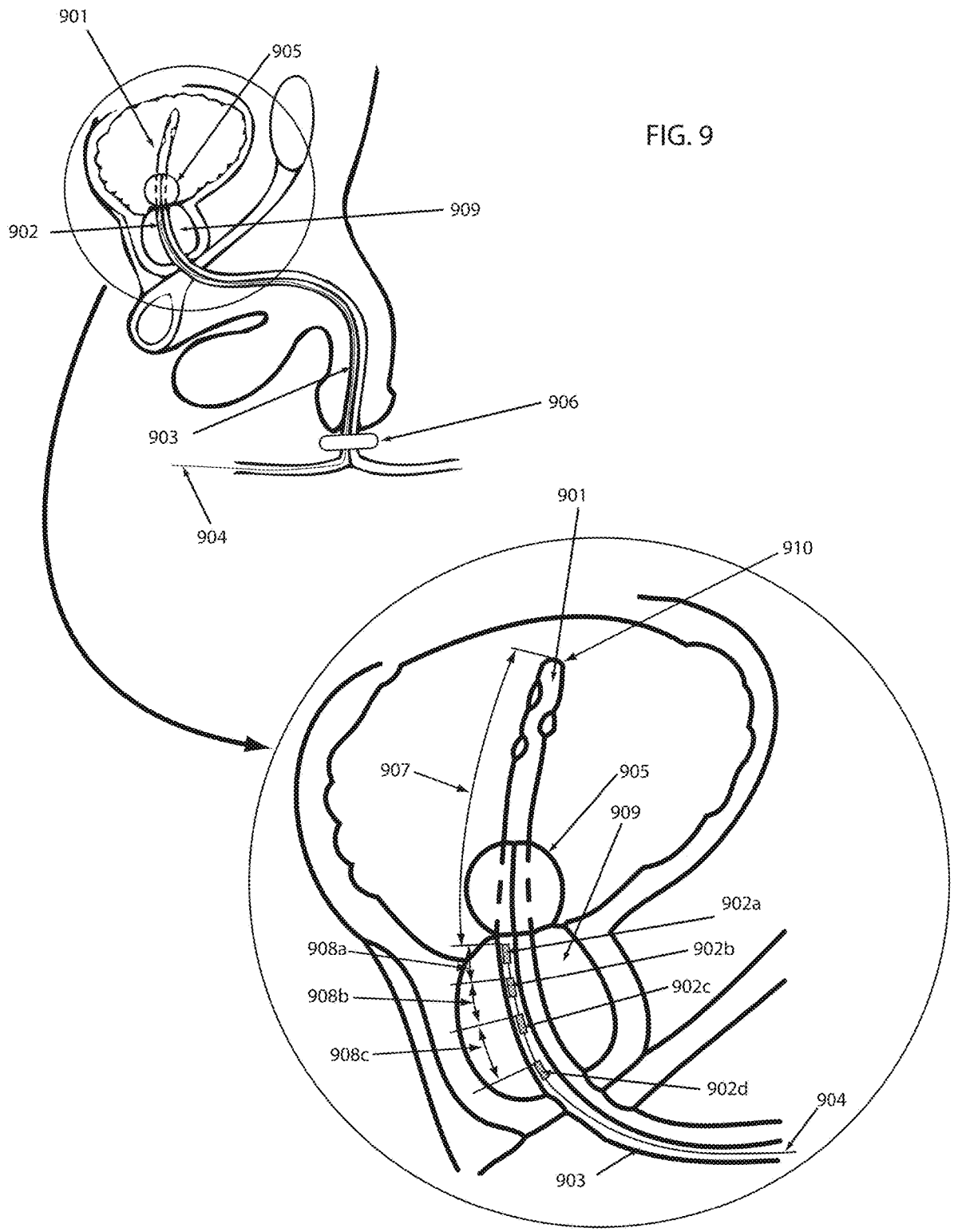
FIG. 9 is an example depiction of a catheter including a position-indicating element that can be used to track motion of a tissue or organ, in accordance with one or more implementations of the invention.

FIG. 9 is an example depiction of a catheter including a position-indicating element that can be used to track motion of a tissue or organ, in accordance with one or more implementations of the invention. Although described in terms of a prostate procedure, it is understood that the techniques described herein are equally applicable to many other procedure types.

In an implementation, a catheter 901 (e.g., a Foley catheter) may be positioned in a patient and the integrated balloon inflated as indicated in FIG. 9. The inflation balloon 905 normally used to retain the catheter may also serve to immobilize the catheter in the prostate. A dual balloon Foley catheter such as a Coleman or Lerman catheter (C.R. Bard, Inc., Murray Hill, N.J.) may also be used (not shown). One balloon may be inflated in the urethra to restrain it, while the second may be inflated at the bladder neck. In some nonurologic situations, a non-occlusive restraining mechanism may be employed such as those described in U.S. Pat. No. 6,785,571. In a variation, another restraint, balloon, collar, clip, locking device or clamp, etc. 906, may be applied externally at the exit point of the catheter to help immobilize catheter 901 from moving longitudinally. The flexible catheter 901 may also include an interior lumen that may receive an elongated medical instrument to perform a diagnostic or therapeutic function and may include biopsy devices, imaging devices, ablation devices, beams of light or radiation (e.g., laser or radiation delivered by a catheter), scalpels, needles, temperature sensors, electrodes, forceps, brushes, and/or other type of elongated medical instrument.

In an implementation designed to track the motion of the tissue or organ for gating, the Foley catheter above may be equipped with at least one position indicating element. This would enable the catheter to be used in order to track the repeated motion of the tissue during the procedure caused, for example, by respiration. In some instances the position indicating element may be designed to be tracked by a position sensor but in others, it may be a passive component such as a fiducial that is visible to an imaging modality such as x-ray.

In an implementation designed to track the motion of the tissue or organ for dynamic referencing or for gating, the Foley catheter above may be equipped with at least one six-degree-of-freedom position indicating element or two five-degree-of-freedom position indicating elements. This would enable the catheter to be used in order to track the location of the prostate during the procedure in cases where the catheter is parked so that the sensors are placed in the prostatic urethra. Here the term "parked" refers to a fixation of the catheter and thus the position indicating elements in a particular location of the anatomy during the data collection In an implementation, designed to perform the triple function of gating, dynamic referencing, and registering the Foley catheter above may be equipped with at least two longitudinally displaced five, or six degree-of-freedom position indicating elements (or a combination of a five and a six degree-of-freedom elements). Again this may be accomplished by parking the catheter so that the sensors are within the prostate in the prostatic urethra.

In the implementation illustrated in FIG. 9, catheter 901 may include a position-indicating element 902. In an implementation shown in the inset of FIG. 9, a plurality of position indicating elements 902a, 902b, 902c, and 902d may, for example, be included within catheter 901. The position, and possibly orientation of position, indicating elements 902 (i.e., 902a-902d) may be located using a tracking device for purposes of gating, dynamic referencing, and registration as detailed above. In an implementation, the position-indicating elements may be attached within one of the existing lumens of the catheter, such as a balloon inflation lumen, the drainage lumen, or in an irrigation lumen of a three lumen catheter, or in a special dedicated lumen, here indicated as 903. In an implementation, the position indicating elements are disposed to be retained substantially within the tissue of interest during the procedure, here within the prostate 909, and therefore proximal to the fixation balloon. In an implementation, the position indicating elements are longitudinally displaced relative to one another and their location may be known in the catheter relative to either the tip (distal end) 910 or start (proximal end) of the catheter i.e. distances 907, 908a, 908b, and 908c are known which represent the distance from the start of each sensor to either the tip or start of the catheter. Alternatively, their locations relative to the balloon 905, tip or start of the catheter may be known.

In a similar manner, the position indicating elements along with electrical or optical cables 904 may be removably inserted into a lumen. The position-indicating elements may be inserted into lumens of catheter before or after the catheter has been placed rather than being integrated in the catheter. For example they may be contained within a tube that is removably inserted into the catheter. In doing so, the ultimate location of the position indicating elements within the catheter may be known.

In an embodiment, the catheter has distance markings on it so that the depth of insertion can be determined by reading the markings exterior to the patient. In this way, with knowledge of the catheter geometry, the location of the position indicating elements from the entry point of the catheter can be determined.

In an embodiment where the sensors are permanently fixed to the catheter, the fiber or cable connecting the position indicating elements to the position sensor within the catheter has some amount of slack to it so that if the catheter is stretched, the cable or fiber within does not break.

Methods of Use

In using these devices, the first step is to obtain the path of the registration conduit in image space. This may be done by manually segmenting the conduit from sequential images, or automatically using, for example, a machine learning method such as a convolutional neural network trained to identify the path of the conduit.

Figure 10:
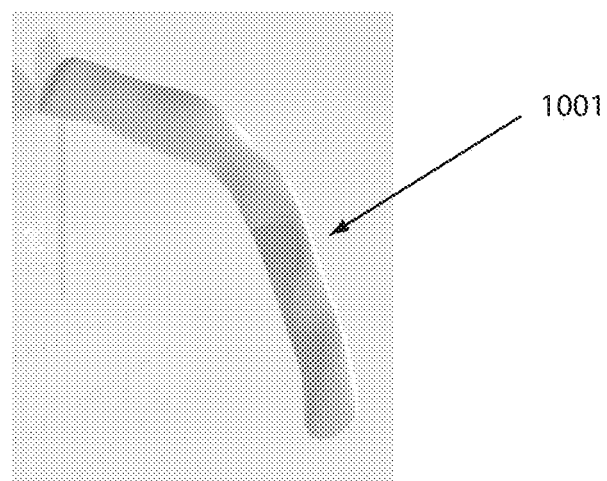
FIG. 10 is an example depiction of a segmented lumen and skeletonized path of its centerline, in accordance with one or more implementations of the invention.
Figure 10:
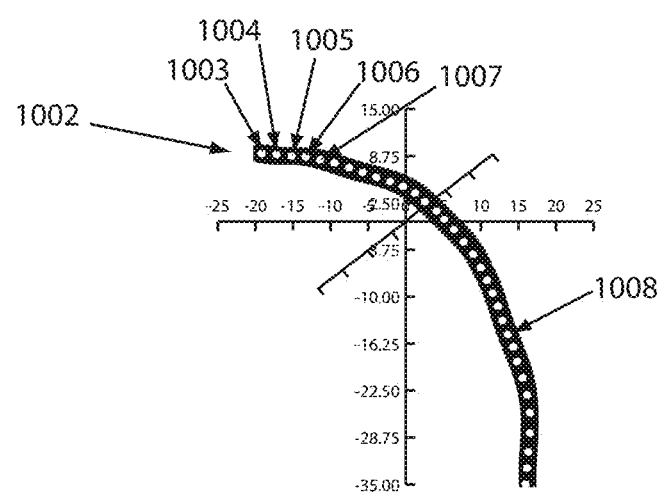

Such a segmentation is illustrated in FIG. 10 as item 1001. The segmentation typically forms a solid object and the centerline, 1002, may be obtained by skeletonization of the segmented images or by using tubular structure centerline algorithms that are known in the art (e.g. Tagliasacchi, A., Alhashim, I., Olson, M., and Zhang, H. 2012. Mean Curvature Skeletons. *Comput. Graph. Forum* 31, 5 (August 2012), 1735-1744. DOI: 10.1111/j.1467-8659.2012.03178.x). Paths are typically expressed as a set of (x, y, z) coordinates of the centerline of the conduit but other methods of expressing it are possible (e.g., piecewise splines and/or other methods of expressing paths). In this figure, a few of the points that comprise the path are depicted as the white circles indicated by numerals 1003, 1004, 1005, 1006, 1007, and 1008, each of which has its own (x,y,z) coordinates so as to comprise a list of coordinate sets. Many such points may exist to describe the centerline.

The imaging step may be further assisted to render the path of the registration conduit more visible by equipping it with one or more fiducials prior to imaging. Fiducials may take the form of points of material, such as small balls. They may also take the form as segments of material such as short wires or tubes. They may be position indicating elements such as electromagnetic sensors or shape sensing optical fibers that happen to be visible on the imaging modality. They may also be a continuous fiducial such as a length of wire, fiber, or filling material. These may be inserted either directly into the conduit at the time of imaging or into a lumen (permanently or removably) into another device such as a catheter or Foley catheter or may be incorporated directly into the structure of the catheter through the selection of specific materials that are intrinsically visible on the imaging method. The location each fiducial relative to the catheter (if used) may be known.

Calculating Initial Registration

Method 1: Sampling Sensors and Using ICP

Referring back to FIG. 9, in an implementation, a catheter 901 such as the one depicted in the inset of FIG. 9 that includes multiple position indicating elements (902a, 902b, 902c, 902d) may be used to perform a patient-to-image registration. This can be done if a pre-procedure image set (such as an MRI) of the path into which the catheter is inserted is available, and details of the construction and placement of each of the multiple position indicating elements is known, but the location of the catheter in the conduit is not. A position sensor is used to sample the patient space locations of the position indicating elements inside of the measurement device that follow the path of the conduit. All that is required is to use a generalized registration method such as ICP to calculate a registration transformation matrix between the patient space locations of the position indicating elements and the image space coordinates of the complete path, with a best fit solution for the registration resulting. This technique may lead to errors in the registration transformation if the path is not sufficiently tortuous (see section Improving Registration below).

Method 2: Parking Catheter at an Assumed Location

The positions in which each position-indicating element (902a, 902b, 902c and 902d) has been secured in catheter 901 is known relative to catheter tip 910 and balloon 905 of catheter 901 at the time of manufacture. When catheter 901 is inserted into the patient and balloon 905 is inflated, the approximate location of each position indicating element within the pre-procedure images of the prostate may be deduced because linear displacement of each position indicating element is known since balloon 905 is lodged against the bladder neck. As before, the path of the urethra and thus catheter 901 is known from an MRI, ultrasound, or other diagnostic scan since the path of the catheter is constrained to the lumen visible on the images. The locations of the position indicating elements are sampled and transformation is calculated assuming an initial parked positioning of the catheter.

Method 3: Measuring Catheter Outside Patient

Figure 11:
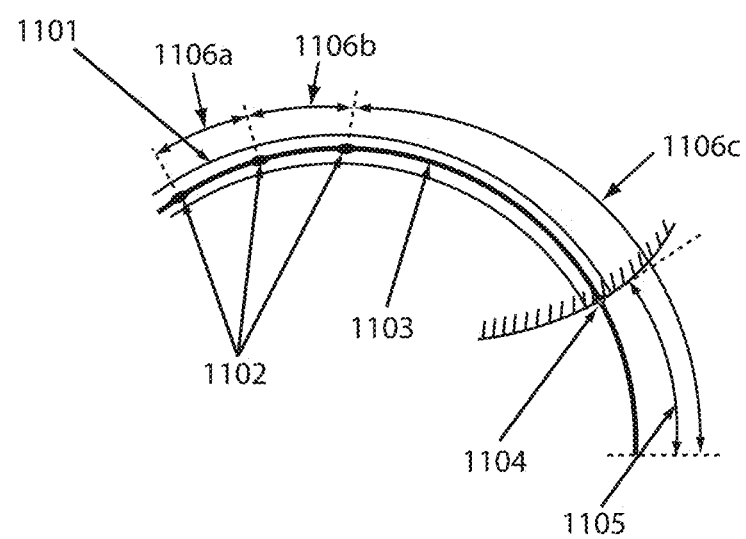
FIG. 11 depicts a urethra and position indicating elements inside a catheter placed in the urethra, in accordance with one or more implementations of the invention.

This is illustrated in FIG. 11 which shows a conduit 1101 and position indicating elements 1102 inside a catheter 1103 placed in the conduit. The catheter exits the patient at point 1104. By measuring the length of the catheter outside of the patient (1105), and with the knowledge of the locations the position indicating elements were placed in at the time of manufacture (1106a, 1106b, and 1106c, for example), then the locations of the position indicating elements within the conduit in image space may be inferred based on the pre-procedure scan and the knowledge that the catheter is constrained to the urethra. The linear displacement of each position indicating element is known since it is possible to measure the length of the catheter external to the patient (using, for example, a ruler or any measurement marks on the catheter).

Method 4: Determining Catheter Location from Another Position

In an embodiment, if a position indicating element or fiducial is placed in a known location in image space, it is possible that the location of the catheter in image space may be determined relative to that device and the parked position of the catheter determined. For example, if a position indicating element or fiducial is placed at a known distance from say, the start of the prostatic urethra, then by measuring the distance of that position indicating element from one present inside the catheter in patient space, it is possible to determine where the catheter has been parked in the urethra in image space since the measuring device is constrained to the conduit. The position indicating element or fiducial may be placed for example on the skin surface as check fiducial 819 in FIG. 8, or may be interior to the patient. The distance of this fiducial or position indicating element may be known to the start of the prostatic urethra by imaging or other means. When one of the position indicating elements in the catheter is determined to be that same distance, then the catheter may be parked and the location of all the position indicating elements in the catheter will be inferred as they are constrained to the conduit.

In these cases (methods 2, 3 and 4), the precise location of the parked conduit in image space is inferred based on secondary information rather than being known so does not constitute a standard registration procedure as known in the art. Normally, the locations of the position indicating elements are known in image space from, for example, direct imaging of them.

Method 5: Using Imaging to Park Catheter or Determine Parked Position

Locations of position indicating elements relative to the images could of course also be established through the use of imaging devices such as X-ray or ultrasound to assist in parking the catheter at a known location or deriving its location based on adjacent visible features in the images that were present at the time of the scan (e.g. branch points of vessels, proximity to a bone, or proximity to an preplaced fiducial). The presence of cooperative imageable targets such as fiducials on the end of catheter or at the balloon could also assist in positioning the catheter correctly, but again this is an indirect measurement that does not identify the position indicating elements within the catheter directly. Indeed it may be difficult or impossible to image the position indicating elements directly in order to perform the registration, as they would normally be embedded within the catheter and may be invisible using ultrasound for example. Special identifying features may be added to the exterior of the catheter to indicate the locations of the position indicating elements in this case.

Optical imaging techniques can also help locate the catheter. For example, an imaging optical fiberscope or urethroscope inserted into the catheter may assist in locating landmarks in the conduit such as the internal or external urethral sphincters in the urethra, or the carina or various branch points in the bronchial passages, which would determine the location of the catheter in and therefore the position indicating elements. Indeed, it may often be possible to "feel" the sphincters with the catheter during insertion as the elements of the catheter are pushed through them. Ultrasound may devices may include externally placed transducers as well as internal transducers such as transrectal ultrasound (TRUS) and intra-catheter ultrasound devices such as endobronchial ultrasound (EBUS), intravascular ultrasound (IVUS) etc.

Method 6: Determining Catheter Path by Moving or Sliding Sensor

The path of the conduit could equally be determined using a "drag-back" technique using a single sensor that is slid through the conduit or catheter as explained in U.S. patent application Ser. No. 11/059,336 and U.S. patent application Ser. No. 15/281,137 both entitled, "METHOD AND APPARATUS FOR REGISTRATION, VERIFICATION, AND REFERENCING OF INTERNAL ORGANS" by Glossop, both of which are hereby incorporated by reference herein in their entirety. A version of this is also discussed by Donhowe et al. in U.S. patent application Ser. No. 15/752,166 and U.S. patent application Ser. No. 15/752,154, both of which are hereby incorporated by reference herein in their entirety. Again, it would be necessary to assume the location of the catheter in the patient and the extents of the dragging of the sensor in the conduit as this is not taught in the applications.

Therefore, if the path of the urethra or other registration conduit is determined in image space from scans taken prior to the operation, the position and orientation of the position indicating elements within the registration conduit (i.e., prostatic urethra) may be deduced in image space. The locations and orientations of the position indicating elements may be determined by the position sensor in patient space. This allows an "initial registration" to be calculated relating the position indicating elements positions (patient space) and orientations and the assumed positions from the pre-procedure scans (image space). This initial registration may then be used to target any device that contains a position indicating element or improved prior to doing so.

Improving Registration

For various reasons, the initial registration may not be accurate. In various implementations, one or more methods described below may be used to improve the initial path-based registration.

Unless a plurality of conduits are selected, it is preferred that individual conduits have a curvature or tortuosity to them and not be straight or form an arc of a circle. In this latter case, it may not be possible to calculate an accurate registration using ICP alone. This may be the case in the prostate, where the prostatic urethra may roughly follow an arc as indicated in FIG. 10, although not all prostatic urethras are curved in this manner. Likewise, some blood vessels or bronchial passages are virtually straight or form an arc of a circle and may not produce a unique or accurate registration. It may be possible to use a mostly straight or arc shaped conduit if additional registration information such as additional points or paths are used or adjustments are performed. In some embodiments, it may be preferred that multiple position indicating elements be used to better approximate the shape of the conduit.

Figure 12:
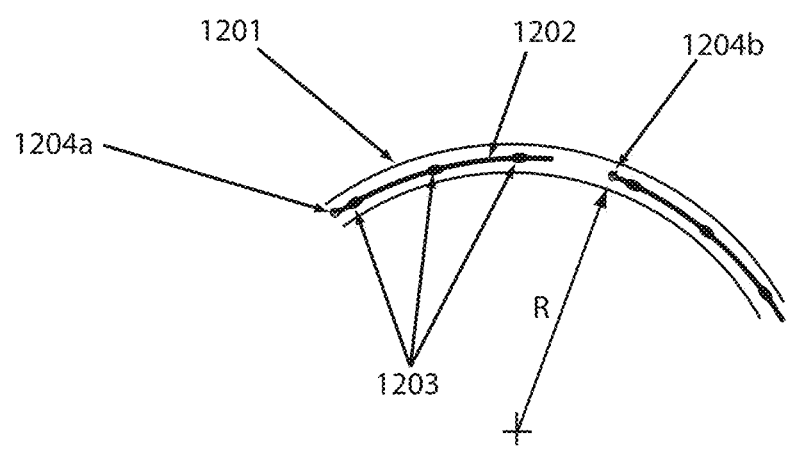
FIG. 12 depicts an example in which position indicating element locations are not known in an image space, in accordance with one or more implementations of the invention.

Unless imaging means can be used to confirm its location, the catheter position may not be precisely known in image space. In this situation, it may not always be possible to obtain an accurate registration, as illustrated in FIG. 12. Here, the conduit or urethra 1201 is shaped as an arc (other shapes that lead to the same outcome are also possible) of constant radius of curvature R. If measurement device 1202 (and thus the position indicating elements 1203) is known to be in the correct location (for example to be placed at location 1204a), then it will be possible to uniquely and accurately register the patient. However, if the catheter is placed at some other location on the arc such so that it starts at 1204b, but assumed to be located at 1204a registration may still also be possible but will lead to incorrect results even though the numerical fit of the registration may indicate it to be accurate. Only if the urethra or conduit is sufficiently tortuous or the starting position is known will an ICP algorithm converge on a unique "correct" solution, otherwise it will result in one of the many possible incorrect solutions, sometimes known as a "local minimum." It is important to be able to detect and correct for this type of error.

Method 1: Optimizing Overlay of Pre- and Intra-Procedural Images

In an embodiment, poor registration may be detectable and corrected by imaging. An imaging device (e.g. a calibrated ultrasound tracked with a position indicating element) may be used to obtain an image of the anatomy after the initial registration. In an embodiment, the preoperative images or segmentations are then transformed to the patient coordinate system using the initial transformation matrix calculated using the catheter registration and the position indicating element on the imaging device. If the two images do not coincide, adjustments are made either manually or using an automated method until a "stopping criterion" is met, which is to produce the maximum overlay of the image with the predicted position of the anatomy based on the position indicating element. These corrections are then applied to the transformation matrix to produce a revised, more accurate transformation matrix.

In an embodiment, this operation may also be performed in order to align check fiducials with the preoperative images of the check fiducials. In addition to directly imaging them in patient space, their location may also be established with a probe or by using "active fiducials." Active fiducials contain position indicating elements that are laid on top of, or are used to replace the check fiducials that were used at the time of imaging. The fiducials incorporating position indicating elements may be replaced at the time of the intervention in the same location as the fiducials imaged prior to the procedure, so there is no need to touch the fiducial with a probe.

The corrections are made in all six degrees of freedom (three rotations and three translations) to align the aforementioned aspects of the images. Note that in this case, the live images (or check fiducial locations) are not used as part of the initial registration calculation, but are used after registration to verify and adjust the registration. The initial registration is modified based on the corrections needed to bring the pre- and intra-procedural images (or segmentations or check fiducials) into concordance. Simultaneous matching in six degrees of freedom can sometimes be time consuming and tedious.

Method 2: Imaging Position Indicating Element Locations

As mentioned, in an embodiment, imaging may indicate the precise positioning of the position indicating elements within the conduit. For example, fiducials visible on the imaging modality may be placed at the location of one or more of the position indicating elements that may be visible using the imager. By locating these relative to the conduit, it may be possible to improve the registration by indicating the actual location of the position indicating elements in the catheter.

Method 3: Adding Points

Additional points not related to the catheter may be obtained from other sources such as surface points or internal points on the patient or organ that may be obtained, for example, by imaging the surface of the prostate with tracked ultrasound, sampling individual points with a tracked probe (e.g., surface points, fiducials), locating them with a fiberscope, and/or by one or more other techniques. These may be used to improve the registration.

Method 4: Minimizing FRE

In an embodiment, incorrect matching may be corrected by adjusting a single parameter (i.e., "s", the initial location of the starting point of the catheter). Since it may be known that the catheter will be constrained to the conduit (e.g., the urethra), adjusting this one parameter may modify the registration in an intuitive manner.

In an embodiment, incorrect matching may be detectable and corrected by calculating the "fiducial registration error" (or FRE), which equals the root-mean-square error in fiducial alignment between image space and physical space. Minimization of the FRE may be possible by systematically and incrementally adjusting the assumed position of the measurement device within the conduit to achieve the best registration. For example, FRE may first be calculated assuming the catheter is at location 1204a and calculating a registration. This position might be obtained by using one of the registration methods above for example. This transformation may be used to calculate FRE. The catheter start location may then be incrementally moved (by a small amount, say "δ") along the path of the urethra (to which it is constrained) to s=position 1204a+δ and FRE calculated again. In an embodiment, δ may be in the range of 0.01 mm to 5.0 mm. This may be repeated several times as the start position s is moved along the path along the conduit, and when FRE is minimized, this may be assumed to be the correct position of the catheter. The calculation of each new s can be done using a variety of techniques besides simply incrementing δ over a range. In some implementations, gradient search techniques or other methods may be used to select an s that minimizes FRE.

Method 5: Minimizing TRE

A similar approach may be carried out by calculating target registration error (or TRE) in evaluating the error of a check fiducial if one is available. TRE may be defined as the distance after registration between corresponding points not used in calculating the registration transform. For full descriptions of FRE and TRE, see Fitzpatrick J M, West J B., The distribution of target registration error in rigid-body point-based registration, IEEE Trans Med Imaging. 2001 September; 20(9):917-27 DOI: 10.1109/42.952729.

In an embodiment, incorrect matching may be detectable and corrected using check fiducials to calculate TRE. A probe, imaging device, or integrated position indicating element may be used to sample one or more check fiducials on the patient and the initial registration applied. In cases where the transformed pre-procedure image of the fiducial and measured patient space (x, y, z) of the fiducial do not coincide, adjustments may be made (e.g., using the incremental method described in Method 4 above or manually or using some other automated method to adjust the assumed starting location (s) of catheter) to produce the maximum overlay of the coordinates of the fiducial in patient space with the transformed position of the fiducial based on the initial image of the fiducial in image space.

Note that, in this case, the check fiducials used to calculate TRE may not be part of the registration calculation, but may be used post registration as an accuracy verification and optimization feature. The registration may be modified based on the check fiducials in order to optimize the overlap of the transformed pre-procedure fiducial position (or segmentation of the fiducial) and live (x, y, z) location of fiducial obtained from the probe or position sensor (i.e., to minimize TRE).

Method 6: Maximizing Overlap

The effect of altering the starting point may be similar to sliding a block along a wire in a manner similar to a "bead maze" toy (see U.S. Pat. No. 5,112,268, which is hereby incorporated by reference herein in its entirety), in which the wire may represent the urethra and the bead may represent the transformed image of the prostate.

Figure 13A:
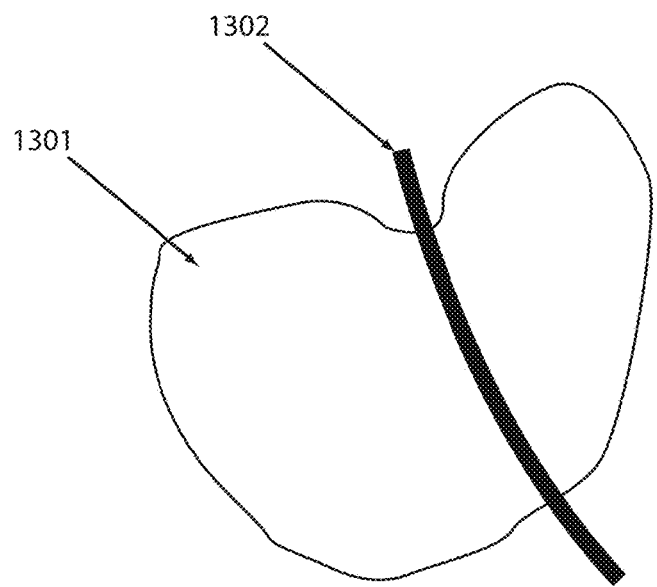
FIG. 13a and FIG. 13b depicts an example image of the potential location of a prostate gland, in accordance with one or more implementations of the invention.

In this case, and with reference to FIG. 13a, the preoperative image or segmentation of the prostate 1301 may be thought of as a solid "bead" that may slide down the urethra 1302 that can be thought of as a "wire." This may be representative of the type of error described earlier in reference to FIG. 12, in which a malpositioned catheter may cause an error in registration.

Figure 13B:
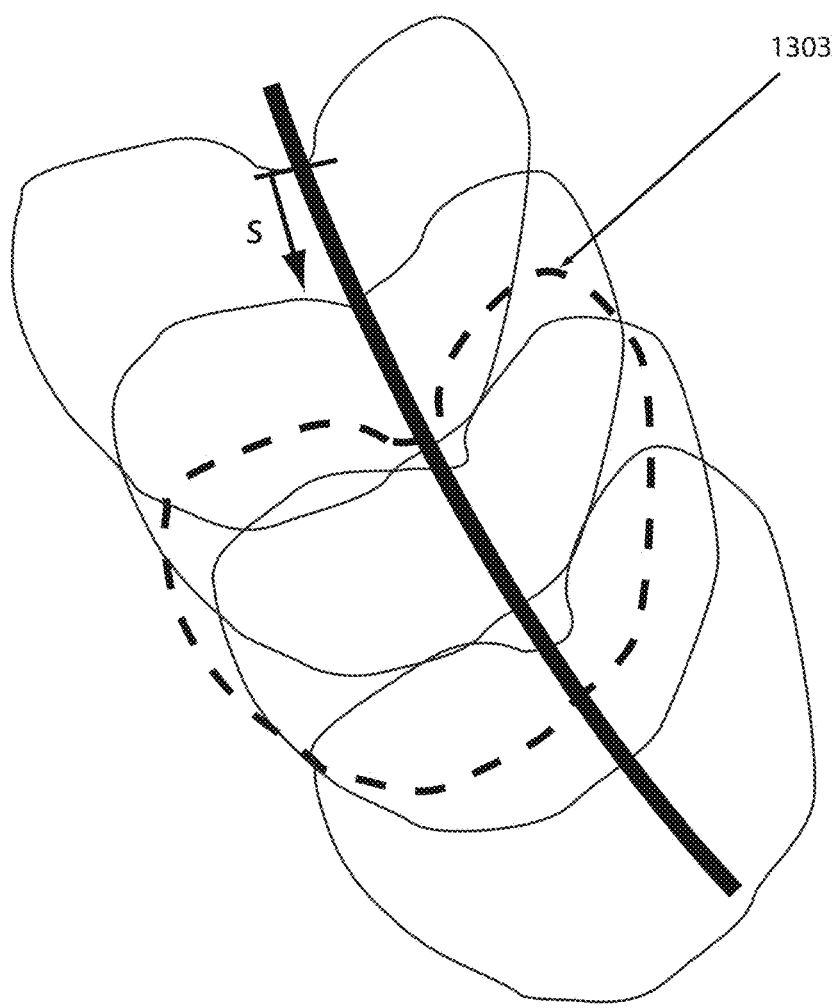

In FIG. 13b, it is shown that by adjusting a single parameter ("s"—the assumed starting point of the catheter in the conduit based on the initial registration), a transformation may be calculated that moves the preoperative images or segmentation of the prostate along the urethral path so that it can be brought into concordance with the live ultrasound image 1303. Likewise, sampled check fiducials can be brought in concordance with the location that was imaged preoperatively. As before, the initial registration may be used and the correction of the registration may be performed afterwards.

EXAMPLE IMPLEMENTATION

By way of illustration of methods 4-6, the segmented urethra or conduit (such as line 1002 of FIG. 10) may be expressed as a list of coordinates (i.e., x, y, z coordinates) representing the path of the centerline of the conduit. In one or more implementations, the list of coordinates may number roughly 100 points, although any number greater than roughly five may be used. An initial registration using three position indicating elements may be performed with the assumption that the first position indicating element in the measuring device is located at for example point 1003, the second is at 1004 and the third at 1005 (the actual points used will depend on the spacing of the position indicating elements and spacing of the coordinates of the path). The object of the adjustment is to determine if by instead assuming the first position indicating element is located at 1004, the second at 1005 and the third at 1006 the overlap of check fiducials or objects is better. The change in start position is the "δ" of method 4, and the new position is "s". The location is then adjusted to 1005, 1006 and 1007 and again checked. When the overlap produced the smallest error, that may be accepted as the best location for the catheter, and the registration from that location may be used.

Example Flowchart for Registration Correction

Figure 14:
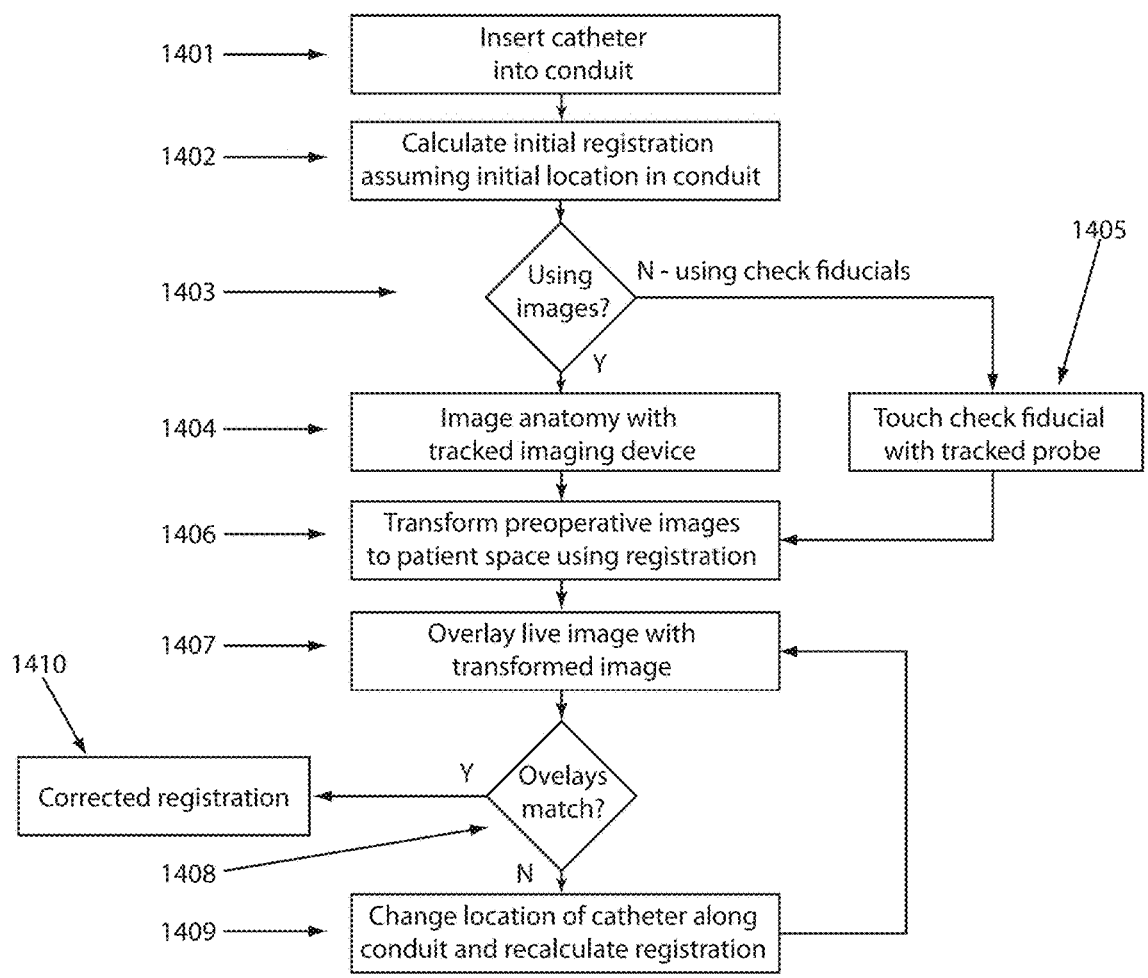
FIG. 14 depicts an example flowchart of the operations required to correct the location of anatomy using live imaging or a check fiducial, in accordance with one or more implementations of the invention.

A sample workflow to correct the registration transformation matrix using methods 4-6 may consist of the following steps that are illustrated in the flowchart of FIG. 14. A similar process applies to registration correction using the other methods.

In step 1401, the catheter or measurement device with position indicating elements may be inserted into the conduit and secured in position.

In step 1402, the initial registration transformation may be calculated using one of the methods described in the section above—"Calculating Initial Registration" (e.g., with the assumption of the catheter's location along the conduit (Method 2) or by measuring the length of the catheter outside of the patient (Method 3)).

If using intra-procedural imaging such as ultrasound with position indicating elements attached to the transducer, decision box 1403 may lead to step 1404. Otherwise, if a probe and check fiducials are used on the patient, step 1405 may be performed.

In step 1404, the anatomy may be imaged with the imaging modality and its location and orientation may be determined from the position indicating elements on the imaging modality (e.g., the transducer handle of an ultrasound).

In the case where one or more check fiducials are used, the location and orientation of a probe containing position indicating elements may be sampled (step 1405) in patient space as it is made to touch a check fiducial on the patient. Alternatively, if the check fiducials have been replaced with fiducials containing position indicating elements, their locations may be sampled in patient space.

In step 1406, the initial registration may be used to transform the preoperative images or segmented regions such as the outline of the prostate or images of the check fiducial determined in image space into the patient space displayed on the live imaging modality. The inverse may also be possible (i.e., transforming the live data into the pre-procedure images).

In step 1407, the intraoperative representation of the anatomy or fiducial may be compared with the transformed preoperative images of the anatomy (or segmented representations of the anatomy) by, for example, overlaying the two image sets (or the live image set with the transformed segmentation), or in the case of fiducials, displaying graphic icons of where the system calculates the fiducials to be located. The comparison may be done visually or an algorithm (e.g., the Dice Similarity Coefficient (DSC) or Hausdorff distance) may be used to score how well the two overlap.

In step 1408, the locations or images may be compared. If the overlays do not match sufficiently, the workflow may proceed box 1410. In the case that they do not overlap well, in step 1409. a correction such as methods 1-6 in the "improving registration" section above may be applied. A user supplied adjustment or automatic adjustment may be applied to the starting location of the catheter "s" in the anatomy, the position indicating elements may be moved along the segmented conduit by this amount, and a new registration matrix may be calculated before returning to step 1407. Once the two images are sufficiently close, the corrected registration matrix may be deemed to have been determined and may be saved as the new registration, as indicated in step 1410.

Although described in terms of position indicating elements, this technique may also be employed when using a measurement device that uses imageable fiducials as well as continuous measuring devices, such as fiber optic shape sensors. In some implementations, this registration method may be used to register anatomy with lumens such as the lungs, and vascularized organs, for example.

Example Flowchart of Complete Procedure

FIG. 15 depicts an example flowchart of the operations required to perform interventions such as therapeutic or diagnostic procedures using the techniques described herein, in accordance with one or more implementations of the invention. Although the procedure is explained using the prostate and urethra, it is understood that the procedure is general and other organs and lumens (both natural such as blood vessels, and those that may be created by the physician) may be used in an analogous manner. In various implementations, steps 1501-1504 may be performed during the preoperative portion of the procedure. Ordinarily a combination of the methods of registration and improvements outlined above may be used together to obtain a sufficiently accurate registration.

In step 1501, an imaging modality such as an X-ray, MRI, CT, ultrasound, CBCT, tomosynthesis, PET, or other imaging modality may be used to obtain one or more two-dimensional (2D) or volumetric images of a patient's anatomy. In some implementations, this may take the form of contrast-enhanced, multi-parametric, or other variation of the scan or scans. The images may be formed into a three-dimensional (3D) image stack which shows details of the anatomy from many slices. Internal or external fiducials, special imageable catheters, etc. if used, should be applied prior to the scan, and the scan should encompass both the fiducials and the anatomy. The imaging modality or at least parts of it (e.g., DWI and/or DCE images in a multiparametric MRI) may render cancerous or other target lesions visible as well as any imaging fiducials. The imaging method may be selected depending on the tissue type, availability, standard of care, and/or one or more other factors. The imagine method may encompass the length of the conduit of interest from entry to target.

In step 1502, the scan(s) may be reviewed by a radiologist or other specialist, or processed by a Computer Aided Diagnosis (CAD) program, or other software (e.g., control application 307). One or more targets may be annotated along with critical structures (e.g., the conduit such as the urethra, nerves, vessels, bones such as ribs, pelvis, etc.). In some implementations, this information (target(s) and structure(s) and/or other information) may be annotated on the images, as a separate list of points and volumes, or stored in a database (or memory) along with other information. Targets may also include a selection of targets designed to represent an orderly and representative sampling through an organ as might be desired during a sextant-style or saturation-style biopsy of the prostate, which aims to sample from throughout the gland. Other targets may cluster more densely around certain structures deemed to be important for either therapy or biopsy such as, for example, local dose boosting around a suspected tumor whilst placing radioactive brachytherapy seeds. Yet another non-limiting example may be an optimized treatment pattern for a large tumor to be treated by multiple successive or simultaneous thermal or cryoablations.

Examples of targets may include locations where biopsies or therapy is desirable. Other examples include locations where critical structures must be monitored (e.g., for temperature, radiation dose, etc.). Other target locations may be used to monitor patient motion such as skin fiducials or localization marks or tattoos. Other targets such as nerves may be locations that must be completely avoided. Other regions of interest are also possible. Regions of interest may be designated at individual points as two dimensional areas, or three dimensional volumes.

In optional step 1503, the scan(s) may be segmented to outline the organ of interest and/or regions of interest (ROI). In some implementations, this information may be annotated on the images, as a separate list of points and volumes, or stored in a computer database (or memory) along with other information. In some implementations, step 1503 may be combined with step 1502. Both the organ and lesions may be segmented to obtain their geometric distribution that may aid in sampling or treating the disease. This may appear as a set of coordinates that may define the outline of the prostate and lesions for example and may aid in visualizing, displaying, planning, and/or performing one or more other operations. This may be done manually or automatically.

In step 1504, the path of a registration "conduit" is obtained in the image space coordinate system from the MRI or other pre-procedure images taken in step 1501. The path of the conduit may also be obtained during the intervention using a real time imaging method such as US, CBCT, or X-ray. Examples of conduits include naturally occurring lumens such as the urethra, bronchial passages, arteries, veins, lymphatic vessels, ureters, biliary ducts, intramedullary canals, the colon, or the small intestine. Artificially created conduits include those that might be created by a physician, such as through the use of inserted or applied needles or catheters. This step may involve determining a centerline from segmented volumes or surface model of the conduit.

The next steps may generally take place at the time of the intervention and may be dependent on the preceding steps being completed.

In step 1505, during the intervention, a measurement device such as a specialized catheter may be inserted into the patient conduit, adjusted, and fixated in place. Examples of measurement devices may include catheters containing one or more position indicating elements (e.g. fiber optic sensors, electromagnetic sensor coils, and/or other types of position indicating elements), catheters containing fiducials (e.g. small balls, short wires, or tubes), reflective objects such as ultrasound emitters or reflectors that may be highly visible under ultrasound, radioactive emitters, or other devices whose position and/or orientation may be determined is introduced into the conduit such as the urethra. The balloon or distal restraint if any (e.g. item 905 of FIG. 9) is activated to lock the catheter in position. The proximal restraint device (e.g. item 906 of FIG. 9) if any is activated to prevent the catheter from sliding.

In an embodiment, the measurement device may be adjusted to a known position (or a position that can be deduced or measured) within the conduit, so that the locations of the position indicating elements within the measurement device in image space may be inferred. Because the location of each position indicating element within the measurement device is known at the time of manufacture, if at least one position along the measurement device is known in the image space, the positions of the rest of the position indicating elements in image space may be calculated since the measurement device may be assumed to be constrained to the conduit.

In an embodiment, the catheter described in step 1505 may contain fiducials that are registered to the patient and may be imaged during the intervention using an ultrasound, X-ray, CBCT, CT, MRI, and/or using one or more other imaging techniques. These fiducials may be present instead of or in addition to position indicating elements, and may be the same as position indicating elements.

In another embodiment, the fiducials or position sensing elements may be removably inserted into a known location in the catheter by temporarily inserting a tube, fiber, bundle, or wire containing the position sensing elements or fiducials into the catheter. In this case, the location of the inserted position indicating elements must be repeatable and known from manufacturing specifications.

In step 1506, the position indicating elements or fiducials in the catheter is used to determine points along the path of conduit in the patient space. Both the position and orientation of the sensors or fiducials may be used if available to approximate the path of the conduit. For example, known methods such as Hermite splines may be constructed to approximate the shape of the catheter from the position and orientation information. In an embodiment, the orientation of the position indicating elements may be taken into account by determining two or more points along the position indicating element (e.g., the beginning and end of the element) based on its position and orientation and assuming the position indicating element (e.g. an electromagnetic sensing coil) is a line. If only position information is available, these points may be used as positions along the path of the conduit.

In an embodiment, the path of the conduit may be obtained by imaging means alone, such as through the use of a tracked ultrasound in which the coordinates of the conduit are able to be determined in the patient space. This may be done with or without the use of the catheter from step 1505 and may be combined with use of position indicating elements as indicated above. In this case, the imaging modality must be calibrated to enable the determination of imaged points in the patient space using a method like Gee et al. previously referenced.

In step 1507, a registration is performed by correlating the conduit or its centerline obtained from the pre-procedure images of the path in image space with path obtained in step 2606 in patient space. One of the methods previously described for obtaining an initial registration may be used.

It may be required that the conduit maintain its path from the time of imaging until the time of intervention. If the conduit changes path after imaging, it may not be possible to use it for registration unless additional registration information such as additional points or paths are used or more advanced non-rigid registration methods are employed. For example, the prostatic urethra may be constrained to a fixed path by the prostate matrix so while the prostate itself may move, the urethral path is mostly unchanged except for a slight straightening if a stiff catheter is used. In some embodiments, a low durometer (e.g., Shore 20A-35A), thin walled (e.g., <1.0 mm), and/or smaller diameter (e.g., <5.0 mm) catheter may be used to minimize urethral straightening. Paths that change periodically, such as those in the lungs, may be used provided gating or motion tracking of some kind is used.

As mentioned, the transformation matrix obtained using the conduit registration may be augmented and improved through the use of the methods 1-6 above. Other methods of improving accuracy are possible.

In step 1508, the registration may be tested for accuracy. This may be done by imaging the prostate or region of interest (e.g., with tracked ultrasound) and ensuring that the transformed MRI outline of the objects overlay. It can also be done by touching check fiducials using a tracked probe and ensuring that the transformed location of the probe tip conforms to the images of the fiducials. Other methods of verification are also possible (e.g., a redundant "check sensor" in the catheter, direct visualization of structures, etc.). If it is found that the registration is inaccurate, steps may be taken at this point to correct the registration to an acceptable level before proceeding using, for example, the steps for "Improving Registration" listed above or the algorithm described herein with respect to FIG. 14.

In step 1509, a tracked template, or a part thereof, may be placed in the vicinity of the target of interest. In an embodiment, the template may consist of a single channel such as tracked cannula 700 in FIG. 7, an aperture including a multileaf collimator, a laser, a photon or particle beam, a predrilled grid, a custom grid, or a partial grid such as a single line of holes. In some embodiments, the template may be placed internal to the patient. Templates may be of any convenient size or shape and multiple templates may be used at one time.

In some implementations, tracked instruments may similarly be used to accomplish the same task as the tracked templates. In this context, instruments may include needles, biopsy devices, drills, electrodes, lasers, radiation therapy devices (and/or other beams), temperature sensors, forceps, laser fibers, brushes, cryotherapy devices, applicators, catheters, pointers, scalpels, stents, saws, and/or any other medical devices so long as tracking devices (i.e., position indicating elements or fiducials) have been attached rendering them able to be tracked by a position sensor. Although referred to as "templates", it is understood that instruments may also be used in the manner described herein. Instruments (such as those listed above) without any integrated tracking may of course be used together with templates that do contains integrated tracking to accomplish the same task (e.g. inserting a biopsy device through a tracked cannula template).

The location and orientation of the template (or instrument) may be obtained as indicated in step 1510. In some implementations, this may be done using the same position sensor as used to determine the conduit path of step 1506 (if the template is equipped with position indicating elements), or fiducials placed on the template may be used in conjunction with the imaging method used if an imaging method is used to determine the position and orientation of fiducials that may be present in the catheter.

Using the transformation matrix calculated in step 1507, the location and orientation of the lesions determined in image space may be obtained in patient space so that all targets are known in the coordinate system of the template as indicated in step 1511. Conversely, using the inverse transformation matrix, the template location and orientation in patient space may be expressed in image space if desired.

In step 1512, the template may be adjusted to ensure at least one of the existing template paths or possible template paths (in the case of a custom template) intersects or passes close to a target selected in step 1502.

In step 1513, paths for instruments, beams, etc. are selected through the template to intersect the lesions. In embodiments where the template contains predrilled paths, a path is selected from the available paths that causes the instrument to approach as closely as possible one or more of the targets identified in step 1502. In situations where a custom template is desired, paths may be specified by a manual or automatic method and manufactured as described previously. The insertion depth of the instruments are calculated at this step. Additional holes may be selected for the purpose of monitoring or augmenting the initial therapy hole. For example, adjacent holes may be selected for inserting temperature or impedance sensing devices to measure the progress of the therapy or for inserting additional therapy needles through to increase the dimensions of the applied therapy.

In step 1514, the template location or the selected path may be modified based on continuously monitoring of the location of the conduit. If the conduit position or shape changes and is detected by imaging or position sensor means, then the user may be alerted and given instructions to adjust the location of the patient, template or selected instrument path to account for the change in position and to maintain accuracy. Dynamic referencing or gating may also be activated by using position indicating elements in the conduit or by imaging means (in which an imaging device such as ultrasound, MRI, X-ray, or other imaging device is used to examine the location of the conduit, and or monitor the progress of the intervention). Dynamic referencing or gating is generally a straightforward process once registration has been achieved using this technique as the same catheter can perform both functions. As described previously, dynamic referencing and can compensate for rigid motion of the object (i.e. translation and rotation of the organ) and can extend to modification of the image space shape of the organ. As such, it is possible to reassign the location of the target based on the position of the path obtained in image space. In this case, methods such as finite element modeling may be used in which the changed position and orientation of the conduit is propagated through the organ and used together with the material properties of the organ to derive new locations of the targets without directly visualizing their changed positions, but only that of the conduit.

In step 1515, instruments for therapy, diagnostics or monitoring may be inserted through the selected paths in the templates to the targets, or in the case of tracked instruments, may be inserted or applied directly.

OTHER FEATURES

In one or more embodiments, a catheter and "proxy" position indicating elements may be introduced during the scan so as to reproduce the conditions that will be seen at the time of the intervention (e.g., in changing the path of the conduit due to the rigidity of the catheter). Likewise, a proxy TRUS probe may be introduced at the time of the scan to occupy the space and effect the deformations that may be apparent at the time of the intervention.

In one or more embodiments, it is possible to determine the image space location by imaging. For example, to register a vessel, contrast may be injected into the vessel, and the catheter may be moved until it reaches a preselected location. It may be possible to also place or tattoo a fiducial onto the skin so that it may be localized by X-ray, and the catheter may be moved to that location. Other sensors may be present in a catheter for blood pressure, temperature, pressure, radiation, and/or other measurements.

The foregoing has been illustrated substantially in terms of a Foley catheter, but could be any type of catheter, including vascular catheters, biliary catheters, or ventricular catheters. It could also be performed using guidewires, needles, and/or other similar instruments, and could be in any organ, not just prostate (e.g., the heart, liver, lung, brain, pancreas, and/or other organ).

In one or more embodiments, the physician may also add random or non-random surface points or an ultrasound sweep with a tracked ultrasound on the prostate. This may augment any registration obtained by the Foley registration. In some embodiments, a deformable registration may be added to better align the prostate imaged using ultrasound with the segmented MRI. The location of a band or area on the catheter may also be imaged to obtain a known point (e.g., take an X-ray or ultrasound to determine the location of the tip in the vessel).

Following registration, position indicating elements or fiducials in the immobilized catheter may be used to dynamically reference the tissue and, by looking for repeated patterns, can be used to gate the intervention.

In an embodiment the catheter may be used to locate critical structures such as the neurovascular bundle and assist in locating it during radical prostatectomy in order to preserve it during the procedure.

Other implementations, uses and advantages of the invention will be apparent to those skilled in the art from consideration of the specification and practice of the invention disclosed herein. The specification should be considered example only.

What is claimed is:

1. A method of performing a guided interventional medical procedure using a template, the method comprising:
   obtaining at least one medical image of a patient's anatomy;
   identifying a location of at least one target in the at least one medical image, wherein the at least one target is identifiable in the at least one medical image that is involved in the guided interventional medical procedure;
   determining a path of at least one conduit in the patient on the at least one medical image in image space, wherein the path of the at least one conduit in image space is expressed based on a coordinate system of imaged data, wherein the imaged data is obtained from the at least one medical image;
   determining the location and/or orientation of one or more position indicating elements affixed to at least one measuring device relative to the at least one measuring device;
   inserting and fixing the at least one measuring device into the at least one conduit;
   assuming an initial location of the at least one measuring device within the at least one conduit;
   determining the location and/or orientation of the one or more position indicating elements affixed to the at least one measuring device relative to at least one tracking device;
   determining a path of the at least one measuring device in a coordinate system of the at least one tracking device using the determined location and/or orientation of the one or more position indicating elements affixed to the at least one measuring device;
   registering the path of the at least one conduit in image space to patient space by mapping the path of the at least one conduit in image space to the path of the at least one measuring device in patient space;
   modifying the initial assumed location of the at least one measuring device and re-registering the path of the at least one conduit in image space to patient space until one or more criteria are met;
   positioning the template near the organ involved in the guided interventional medical procedure;
   determining a position and orientation of the template in patient space;
   transforming the position and orientation of the template in patient space to a position and orientation of the template in image space based on the registration;
   calculating a transformation that moves one or more pre-procedure images to multiple locations along the path of the at least one conduit;
   improving registration by determining the location of the multiple locations that maximizes overlap of information derived from the one or more pre-procedure images and corresponding information obtained during the procedure;

adjusting the position and orientation of the template to ensure a path aligned with at least one channel of the template intersects the at least one target; and placing at least one instrument through the at least one channel in order to provide therapy or receive diagnostic or accuracy information related to the at least one target.

2. The method of claim 1, wherein the at least one measuring device comprises a catheter, a needle, or a guidewire.

3. The method of claim 1, wherein the assumed initial location of the at least one measuring device is obtained by measuring a length of the at least one measuring device exterior to the patient.

4. The method of claim 1, wherein the initial assumed location of the at least one measuring device is obtained by determining a proximity of the at least one measuring device to at least one position whose location is known.

5. The method of claim 1, wherein the initial assumed location of the at least one measuring device is obtained by using imaging to determine the location of the at least one measuring device.

6. The method of claim 1, wherein registering the path of the at least one conduit in image space to patient space comprises registering the one or more position indicating elements in image space to patient space based on the determined location and/or orientation of the one or more position indicating elements in image space and the location and/or orientation of the one or more position indicating elements obtained via the position sensor.

7. The method of claim 1, wherein improving the registration further comprises:

adding registration points where the patient space registration points are obtained from a source other than the at least one measuring device to augment the registration.

8. The method of claim 1, wherein the one or more criteria comprise reaching a minimum target registration error of at least one check fiducial.

9. The method of claim 1, wherein the one or more criteria comprise reaching a maximum overlap between a transformed image and a live image.

10. The method of claim 1, wherein the one or more criteria comprise reaching a minimum fiducial registration error.

11. The method of claim 1, wherein a spatial location and/or orientation of one or more fiducials affixed to the at least one measuring device is known relative to the at least one measuring device, and wherein determining the path of the at least one conduit in patient space comprises:

determining a location and/or orientation of at least one of the one or more fiducials using imaging means.

12. The method of claim 11, wherein the one or more fiducials include point fiducials, straight segments, and/or a fiducial that fully opacifies the at least one conduit.

13. The method of claim 1, wherein the position and orientation of the template in patient space is determined using imaging means.

14. The method of claim 1, wherein the template includes one or more position indicating elements, and wherein determining the position and orientation of the template in patient space comprises:

obtaining, via a position sensor, a location and/or orientation of the one or more position indicating elements of the template.

15. The method of claim 1, wherein the template includes one or more fiducials, and wherein determining the position and orientation of the template in patient space comprises:

determining a location and orientation of the one or more fiducials using imaging means.

16. The method of claim 1, wherein the template is pre-manufactured with one or more channels configured for one or more instruments to pass through, the one or more channels including the at least one channel.

17. The method of claim 1, the method further comprising:

registering a position of the at least one measuring device in image space to patient space, wherein the at least one measuring device is used to dynamically reference the at least one target.

18. The method of claim 1, wherein the at least one conduit whose shape is used for registration includes a curved conduit, an artery, a vein, a lymphatic vessel, a urethra, a ureter, a bronchus, a biliary duct, a medullary canal, a colon, a small intestine, or an artificially created conduit.

19. The method of claim 1, wherein the assumed location of the at least one measuring device is obtained by fixing the end of the at least one measuring device at a known location.

20. The method of claim 1, wherein the maximizing overlap comprises visually inspecting the transformed locations of one or more features that may include fiducials, bones, contours, conduits or other anatomical features.

21. The method of claim 1, wherein the maximizing overlap comprises calculating using one or more measurement criteria that include Dice Similarity Coefficient (DSC) or Hausdorff distance.

22. The method of claim 7, wherein the added patient space points are surface or internal points obtained by one or more of: a tracked probe, a tracked ultrasound, or a tracked fiberscope.

23. The method of claim 1, wherein the at least one target is an externally placed fiducial, and the accuracy information is related to the distance of the instrument tip to the external fiducial.

24. The method of claim 1, wherein modifying the initial assumed location of the at least one measuring device and re-registering the path of the at least one conduit in image space to patient space until one or more criteria are met comprises:

modifying the initial assumed position of the measuring device such that it is constrained along the path of the at least one conduit and re-registering the path of the at least one conduit in image space to patient space until the one or more criteria are met.

* * * * *